US009314339B2

(12) United States Patent
Mansmann

(10) Patent No.: US 9,314,339 B2
(45) Date of Patent: Apr. 19, 2016

(54) IMPLANTS FOR REPLACING CARTILAGE, WITH NEGATIVELY-CHARGED HYDROGEL SURFACES AND FLEXIBLE MATRIX REINFORCEMENT

(75) Inventor: Kevin A. Mansmann, Paoli, PA (US)

(73) Assignee: Formae, Inc., Paoli, PA (US)

( * ) Notice: Subject to any disclaimer, the term of this patent is extended or adjusted under 35 U.S.C. 154(b) by 1016 days.

(21) Appl. No.: 10/677,444

(22) Filed: Oct. 2, 2003

(65) Prior Publication Data

US 2004/0133275 A1 Jul. 8, 2004

Related U.S. Application Data

(63) Continuation-in-part of application No. 09/818,811, filed on Mar. 27, 2001, now Pat. No. 6,629,997.

(60) Provisional application No. 60/192,482, filed on Mar. 27, 2000.

(51) Int. Cl.
*A61F 2/08* (2006.01)
*A61F 2/30* (2006.01)
(Continued)

(52) U.S. Cl.
CPC ......... *A61F 2/30965* (2013.01); *A61F 2/30756* (2013.01); *A61F 2/3872* (2013.01); *A61L 27/44* (2013.01); *A61L 27/50* (2013.01); *A61L 27/52* (2013.01); *A61L 27/56* (2013.01);
(Continued)

(58) Field of Classification Search
CPC ....... A61L 27/40; A61L 27/52; A61L 27/446; A61F 2/3872; A61F 2/30756; A61F 2/30965; A61F 2002/5055; A61F 2002/30751; A61F 2002/30031; A61F 2002/30673

USPC ................ 623/14.12, 17.11–17.19, 23.72
See application file for complete search history.

(56) References Cited

U.S. PATENT DOCUMENTS 4,195,368 A * 4/1980 Patrichi ............... A61F 2/02
623/14.12
4,502,161 A * 3/1985 Wall .................... 623/14.12
(Continued)

FOREIGN PATENT DOCUMENTS

EP 0677297 A1 10/1995

OTHER PUBLICATIONS

Communication from EPO Examining Division and response in EP 1722717 (appln. nr. 04 79 4020), May 24, 2013.
Supplementary EPO search report in EP 1722717, Jan. 21, 2011.

*Primary Examiner* — Thomas J Sweet
*Assistant Examiner* — Cheryl Miller
(74) *Attorney, Agent, or Firm* — Duane Morris LLP

(57) ABSTRACT

A permanent non-resorbable implant allows surgical replacement of cartilage in articulating joints, using a hydrogel material (such as a synthetic polyacrylonitrile polymer) reinforced by a flexible fibrous matrix. Articulating hydrogel surface(s) are chemically treated to provide a negative electrical charge that emulates the negative charge of natural cartilage, and also can be treated with halogenating, cross-linking, or other chemical agents for greater strength. For meniscal-type implants, the reinforcing matrix can extend out from the peripheral rim of the hydrogel, to allow secure anchoring to soft tissue such as a joint capsule. For bone-anchored implants, a porous anchoring layer enables tissue ingrowth, and a non-planer perforated layer can provide a supportive interface between the hard anchoring material and the softer hydrogel material.

11 Claims, 4 Drawing Sheets

(51) Int. Cl.
*A61L 27/44* (2006.01)
*A61L 27/50* (2006.01)
*A61L 27/52* (2006.01)
*A61L 27/56* (2006.01)
*A61F 2/50* (2006.01)
*A61F 2/38* (2006.01)
*A61F 2/40* (2006.01)
*A61F 2/42* (2006.01)
*A61F 2/46* (2006.01)

(52) U.S. Cl.
CPC .......... *A61F 2/30767* (2013.01); *A61F 2/3804* (2013.01); *A61F 2/40* (2013.01); *A61F 2/4202* (2013.01); *A61F 2/4225* (2013.01); *A61F 2/4241* (2013.01); *A61F 2/4261* (2013.01); *A61F 2002/302* (2013.01); *A61F 2002/30009* (2013.01); *A61F 2002/30014* (2013.01); *A61F 2002/30016* (2013.01); *A61F 2002/30031* (2013.01); *A61F 2002/30034* (2013.01); *A61F 2002/30062* (2013.01); *A61F 2002/30069* (2013.01); *A61F 2002/30131* (2013.01); *A61F 2002/30225* (2013.01); *A61F 2002/30563* (2013.01); *A61F 2002/30673* (2013.01); *A61F 2002/30751* (2013.01); *A61F 2002/30785* (2013.01); *A61F 2002/30787* (2013.01); *A61F 2002/30892* (2013.01); *A61F 2002/30971* (2013.01); *A61F 2002/4631* (2013.01); *A61F 2002/5055* (2013.01); *A61F 2002/5086* (2013.01); *A61F 2210/0004* (2013.01); *A61F 2230/0013* (2013.01); *A61F 2230/0065* (2013.01); *A61F 2230/0069* (2013.01); *A61F 2250/0018* (2013.01); *A61F 2250/0019* (2013.01); *A61F 2250/0028* (2013.01); *A61F 2250/0031* (2013.01); *A61F 2310/00796* (2013.01)

(56) References Cited

U.S. PATENT DOCUMENTS

| | | | | |
|---|---|---|---|---|
| 4,836,884 A | * | 6/1989 | McAuslan | A61L 33/0064 216/83 |
| 4,857,041 A | * | 8/1989 | Annis et al. | 600/30 |
| 4,880,429 A | * | 11/1989 | Stone | 623/14.12 |
| 5,067,964 A | * | 11/1991 | Richmond et al. | 623/14.12 |
| 5,314,478 A | * | 5/1994 | Oka et al. | 623/14.12 |
| 5,658,343 A | * | 8/1997 | Hauselmann | A61F 2/30756 623/23.72 |
| 5,795,353 A | | 8/1998 | Felt | |
| 6,027,744 A | * | 2/2000 | Vacanti | A61F 2/28 424/426 |
| 6,146,655 A | * | 11/2000 | Ruben | A61K 9/006 106/35 |
| 6,264,695 B1 | * | 7/2001 | Stoy | 623/17.16 |
| 6,398,814 B1 | * | 6/2002 | Paasimaa | A61L 31/12 623/23.51 |
| 6,726,721 B2 | * | 4/2004 | Stoy | A61F 2/441 623/17.11 |
| 6,783,546 B2 | * | 8/2004 | Zucherman et al. | 623/17.16 |
| 7,108,721 B2 | * | 9/2006 | Huckle et al. | 623/23.74 |
| 2001/0016772 A1 | * | 8/2001 | Lee | A61L 27/3804 623/14.12 |
| 2002/0022884 A1 | | 2/2002 | Mansmann | |
| 2002/0029083 A1 | * | 3/2002 | Zucherman | A61F 2/12 623/17.16 |
| 2002/0183845 A1 | * | 12/2002 | Mansmann | 623/13.11 |
| 2003/0036801 A1 | | 2/2003 | Schwartz | |
| 2003/0212456 A1 | * | 11/2003 | Lipchitz et al. | 623/13.17 |
| 2004/0070107 A1 | * | 4/2004 | Stoy | 264/232 |
| 2004/0072942 A1 | * | 4/2004 | Chen | B32B 27/00 524/549 |
| 2004/0147673 A1 | * | 7/2004 | Calabro | A61K 47/34 525/54.1 |
| 2004/0195727 A1 | * | 10/2004 | Stoy | 264/319 |
| 2004/0199250 A1 | * | 10/2004 | Fell | 623/14.12 |
| 2005/0043813 A1 | * | 2/2005 | Kusanagi | A61F 2/30756 623/23.58 |
| 2005/0055099 A1 | * | 3/2005 | Ku | 623/17.16 |
| 2005/0171611 A1 | * | 8/2005 | Stoy et al. | 623/17.16 |

* cited by examiner

LEGEND:
- ○ SAPL
- ○ Lubricen
- ∞ Lubricen/SAPL complexes
- ● Hyaluronic acid
- ⊕ Other macromolecules
- ⋲ ⋲ ⋲ Semi-permeable membranes

UNLOADED JOINT SPACE

INSTANTANEOUS LOADING

STATIC COMPRESSION

HYDROPLANING MOTION

LOADED FLUID FLOW THROUGH SELECTIVELY PERMEABLE MEMBRANES

IMPLANTS FOR REPLACING CARTILAGE, WITH NEGATIVELY-CHARGED HYDROGEL SURFACES AND FLEXIBLE MATRIX REINFORCEMENT

RELATED APPLICATIONS

This application is a continuation-in-part of patent application Ser. No. 09/818,811, filed Mar. 27, 2001, now U.S. Pat. No. 6,629,997, which in turn claimed the benefit of provisional application 60/192,482, filed Mar. 27, 2000.

FIELD OF THE INVENTION

This invention relates to surgical implants that are designed to replace hyaline cartilage segments having smooth articulating surfaces, in mammalian joints such as knees, hips, shoulders, etc. These implants fall into the category of non-resorbable synthetic implants that will permanently replace cartilage; such implants are entirely different and distinct from resorbable implants that are designed to shelter and protect transplanted cartilage-generating cells while the cells generate new cartilage.

BACKGROUND OF THE INVENTION

The structure and components of soft tissues are discussed in nearly any textbook on human physiology (e.g., Guyton and Hall, *Textbook of Medical Physiology*, 9th edition (1996) at page 186). Very briefly, the cells in most types of "soft tissue" (excluding bones, teeth, fingernails, etc.) are held together by a matrix (i.e., a three-dimensional network) of two types of fibers.

The larger and stronger type of fiber is collagen, a well-known fibrous protein that provides most of the tensile strength of tissue.

The other major type of fiber that helps hold together soft tissue consists mainly of "proteoglycan filaments". These filaments contain a small quantity of protein and a much larger amount (roughly 98%) of hyaluronic acid, a natural polymer with alternating saccharide rings of glucosamine and glucuronate. Unlike collagen fibers, which are thick and provide high levels of tensile strength, proteoglycan filaments are extremely thin, and cannot be seen under light microscopes. They cause the watery extra-cellular fluid in soft tissue to form a gel-like material called "tissue gel". This gel contains water, the proteoglycan filaments, and any other extra-cellular molecules that are suspended in the watery solution.

Roughly $\frac{1}{6}$ of the volume of a person's body is made up of tissue gel, and it is essential to proper functioning of any type of soft tissue; among other things, it helps oxygen and nutrients reach cells, it aids in the removal of waste metabolites from tissue, and it helps tissue remain flexible and supple. Because proteoglycan filaments are so thin, molecules dissolved in tissue gel can permeate through the gel material with very little impedance; experiments have indicated that dye molecules can diffuse through tissue gel at rates of about 95 to 99 percent of their diffusion rates in water or saline.

Because nearly any type of soft tissue, in its normal and natural state, can be regarded as a type of hydrogel, many efforts have been made to create and use synthetic polymeric hydrogel materials as tissue implants. Most of these polymers are created by using non-parallel strands of long organic polymeric molecules (usually with chemical structures that are easier to work with and manipulate than glucosamine and glucuronate). Such molecules, to be suitable for use in a hydrogel, must be very hydrophilic (i.e., they must be able to attract and hold large quantities of water). This is most frequently accomplished by polymerizing precursor molecules that will provide large numbers of hydroxy groups (or other hydrophilic groups), on relatively short "side chains" or "side groups" that are bonded in a regular spaced manner to the long "backbone" strands of the final polymer.

An example of a synthetic hydrogel of this nature is PHEMA (an acronym for poly-hydroxy-ethyl-meth-acrylate), which is used to make soft contact lenses, drug-releasing hydrogels, and similar articles. In contact lenses made of PHEMA, the polymer does not actually bend light. Instead, the water that dwells inside the PHEMA polymer when the lens is hydrated does that job. The hydrophilic PHEMA polymer merely holds water molecules together, in the shape of a contact lens. If a polymer such as PHEMA is dehydrated, it typically becomes brittle; as long as it remains filled with water, it stays soft and flexible. However, like most synthetic hydrogels, PHEMA does not have sufficient strength and durability to last for years (or decades) as a permanent surgical implant.

PHEMA is not the only synthetic polymer used to create biocompatible hydrogels; other polymers that can swell and soften when saturated with water include various hydrophilic polyurethane compositions (e.g., Gorman et al 1998 and U.S. Pat. No. 4,424,305, Gould et al 1984), poly(vinyl alcohol) compositions (e.g., Wang et al 1999), polyacrylonitrile compositions (e.g., U.S. Pat. No. 4,420,589 (Stoy 1983) and U.S. Pat. No. 4,493,618 (Stoy et al 1990)), and other compounds known to those skilled in this field of art.

The flexible, pliable, gel-like nature of a water-saturated synthetic hydrogel arises mainly from crosslinking attachments between non-parallel fibers in the gel. Depending on the specific polymeric structure that has been chosen, the crosslinking attachments between the long "backbone" chains in a hydrogel polymer can be formed by covalent bonding, by hydrogen bonding or other ionic attraction, or by the entanglement of chains that have relatively long and/or "grabby" side-chains or groups. Regardless of which type of bonding or entangling method is used to hold the polymeric chains together in a hydrogel, the "coupling" points between the chains can usually be flexed, rotated, and stretched.

In addition, it should be recognized that the backbone chains in hydrogel polymers are not straight. Instead, because of certain aspects of interatomic bonds and the "tetrahedral" arrangement of the electron pairs in the valence shells of carbon atoms, the long backbone chain of a polymeric molecule will be kinked, and can be stretched somewhat, in an elastic and springy manner, without breaking the bonds.

In a typical hydrogel, the fibers take up only a small portion of the volume (usually less than about 10%, and many hydrogels contain less than 2% fiber volume). The large majority (usually at least 90 to 95%) of the volume is made up of "interstitial" spaces (i.e., the unoccupied spaces that are nestled within the three-dimensional network of fibers, and that become filled with water, when a gel is hydrated). Accordingly, since the "coupling" point between any two polymeric backbone chains can be rotated and flexed, since polymeric backbone molecules can be stretched somewhat without breaking them, and since the water molecules contained in a hydrogel effectively provide a free-flowing lubricant that will not impede relative motion between adjacent polymeric chains, a supple and resilient gel structure is created, when a synthetic hydrogel polymer is hydrated.

Various methods are known for creating conventional polymeric hydrogels. A number of such methods involve mixing together and reacting precursor materials (monomers, mixtures of polymer strands and cross-linking agents, etc.) while they are suspended in water or other solvent. The process of forming cross-linked polymeric strands, while they are suspended in a solvent, can be used to give a desired density and three-dimensional structure to the resulting polymerized matrix. The resulting material is then frozen, to preserve the desired three-dimensional structure of the matrix, and the ice (or other frozen solvent) is then removed, using a process called sublimation or lyophilization. This process uses a combination of freezing temperature and intense vacuum, to cause the frozen solvent to vaporize without passing through a liquid stage, since passage through a liquid stage might alter and damage the three-dimensional molecular structure that will give the gel its final desired shape, cohesion, and other properties.

After the solvent has been removed, any final steps (such as a final crosslinking reaction, rinsing or washing steps to remove any unreacted reagents, etc.) are carried out. The polymer is then gradually warmed up to room temperature, and it is subsequently saturated with water, to form a completed hydrogel.

These and other methods for creating synthetic polymeric hydrogels that are biocompatible and intended for surgical implantation are described in numerous patents, including U.S. Pat. No. 3,822,238 (Blair et al 1974), U.S. Pat. No. 4,107,121 (Stoy 1978), U.S. Pat. No. 4,192,827 (Mueller et al 1980), U.S. Pat. No. 4,424,305 (Gould et al 1984), U.S. Pat. No. 4,427,808 (Stol et al 1984), and U.S. Pat. No. 4,563,490 (Stol et al 1986). In addition, various methods of forming hydrogel coatings on the surfaces of other ("substrate") materials are also described in various patents, such as U.S. Pat. No. 4,921,497 (Sulc et al 1990) and U.S. Pat. No. 5,688,855 (Stoy et al 1997).

There also have been efforts to reinforce some types of hydrogels with an interpenetrating network (IPN) of fibers, to enhance and strengthen a hydrogel's mechanical properties. These reinforcing fibers are usually either chopped into fragments, or longitudinally aligned with the fibers within the hydrogel. A number of these efforts to develop "composite hydrogels" apparently have focused on attempts to create synthetic pericardial tissue (i.e., the membrane that surrounds the heart); see, e.g., Blue et al 1991 and Walker et al 1991. Articles which describe these and other efforts to develop "composite" hydrogels that can be surgically implanted in humans are discussed in two review articles, Corkhill et al 1989 and Ambrosio et al 1998.

As used herein, all references to "implants" or "implantation" (and all terms such as surgery, surgical, operation, etc.) refer to surgical or arthroscopic implantation of a reinforced hydrogel device, as disclosed herein, into a mammalian body or limb, such as in a human patient. Arthroscopic methods are regarded herein as a subset of surgical methods, and any reference to surgery, surgical, etc., includes arthroscopic methods and devices. The term "minimally invasive" is used occasionally, but it is imprecise; one should assume that any surgical operation will be done in a manner that is minimally invasive, in view of the status and needs of the patient, and the goals of the surgery.

Fibro-Cartilage Implants in Spinal Disc Repair

One subset of efforts to develop composite implants with embedded fibers merits attention, but only to point out that it is not relevant to this invention.

A number of researchers have attempted to develop improved fiber-reinforced hydrogel materials, for use in making artificial "intervertebral discs", for repairing or replacing damaged spinal discs. Those efforts are not relevant herein, and the reasons for that exclusion should be recognized, for a better understanding of this invention.

Briefly, the hard vertebral bones of the spine are separated from each other by somewhat flexible discs. Those discs are made of a type of highly fibrous cartilage that is called "fibro-cartilage" in most medical texts (although some books, articles, and patents refer to hyaline cartilage on vertebral discs). The fibro-cartilage material in spinal discs is very different from the type of cartilage that provides the smooth sliding surfaces that cover the sliding ends of bones in joints such as knees, hips, shoulders, etc.

The fibro-cartilage material found in spinal discs must be able to flex, compress, and rotate somewhat, when a person bends over or twists his body. However, spinal discs do not have smooth, slidable, lubricated, articulating surfaces, because they emphatically must not allow any sliding motion to occur, between two adjacent vertebral bones. Instead, one of their primary functions is to totally prevent and prohibit any sliding motion between adjacent vertebral bones. Any such sliding motion, if allowed to occur in the spinal column, would translate directly into shearing motion, and shearing stresses. If allowed to occur in the spine, that type of relative motion between adjacent vertebral bones would pose a grave risk of pinching, injuring, and even shearing (i.e., transversely cutting) the spinal cord.

Therefore, the fibro-cartilage material in spinal discs evolved in ways that prevent sliding motions. Instead of having smooth and slippery surfaces that actively promote smooth sliding motions between adjacent bones, a spinal disc has fibers that extend outwardly from both sides of the disc. Those fibers extend roughly a quarter of an inch into vertebral bones, in a manner that forms transition zones, where fibers from a spinal disc are interlaced with crystals of hydroxyapatite, the calcium-phosphate mineral structure that forms hard bones. Those fiber/mineral transition zones are crucial in reinforcing the attachment of a spinal disc to its adjacent vertebral bones, and in preventing any form of sliding motion that could injure the spinal cord.

Hyaline (or "articulating") cartilage, of the type that covers a bone surface in a joint such as knee or hip, has a totally different structure, because it serves a totally different purpose. Unlike the cartilage in spinal discs, which evolved in ways that absolutely prevent and prohibit any sliding motion, hyaline cartilage in articulating joints absolutely must have at least one smooth and slippery surface, in order to enable the type of sliding motion that occurs in joints such as knees, shoulders, and hips.

Meniscal cartilage (in knee joints) and labral cartilage (in hip and shoulder joints) is in a curious intermediate category. As with hyaline cartilage, meniscal and labral cartilage must provide a smooth and slippery surface, which is specifically designed to promote sliding motion and articulation of those joints. This crucial factor renders meniscal or labral cartilage completely and totally different from spinal discs.

However, it also should be noted that meniscal and labral cartilage have fibrous internal structures, and are usually classified as fibro-cartilage. Unlike hyaline cartilage, they do not form a relatively thin layer that is anchored to a hard bone; instead, meniscal and labral cartilage segments are formed in relatively long semi-circular arcs, which are anchored to bone only through ligaments that extend out of both tips of the arc. Therefore, the internal structure of meniscal or labral cartilage requires high levels of internal fibrous reinforcement. This led to the evolution of fibro-cartilage internal structures. However, as with hyaline cartilage, this fibrous reinforcing structure is covered with smooth and slippery surfaces; accordingly, it is totally different from the fibrous interfaces that must totally prevent any slippage between vertebral bones and spinal discs, in a mammalian spine.

Accordingly, prior art efforts to develop fiber-reinforced cartilage replacements, for use in repairing or replacing spinal discs (as described in various patents such as U.S. Pat. No. 4,911,718, Lee et al 1990, and U.S. Pat. No. 5,171,281, Parsons et al 1992), are worth noting, but only in passing. This current invention has a completely different goal, and a completely different set of physical and performance constraints. Instead of creating spinal disc replacements that will carefully prevent any sliding motion, to avoid shearing stresses on a spinal cord, the goal of this invention is to provide cartilage segments that will provide the exact opposite function: they must have extremely smooth and "lubricious" surfaces, to promote smooth and lubricated sliding motions (also called "articulating" motion) between adjacent bones, in joints such as knees, hips, and shoulders.

The challenge of providing a smooth and lubricated surface, in a surgical implant that will replace a segment of articulating cartilage, can be accomplished most effectively through the use of hydrogel materials. However, hydrogel materials are notoriously weak and easy to damage, due to the fact that they contain a large majority (by volume) of water molecules, and only a small quantity of polymer or protein molecules that will provide the three-dimensional matrix that holds the water molecules inside the hydrogel.

Accordingly, this invention discloses special types of reinforced hydrogel implants having smooth and lubricious surfaces, for replacing cartilage in articulating joints.

Resorbable Versus Non-Resorbable Implants

It must also be recognized that the reinforced hydrogel implants disclosed herein fall into the "non-resorbable" category of cartilage implants. These implants are designed to entirely replace a segment of damaged or diseased cartilage, on a permanent basis. As such, they are designed to remain inside the joint of the patient for multiple years (preferably for the entire remaining life of the patient, if possible).

This trait is important, because it excludes implants that are designed to hold and protect transplanted cells that will generate new cartilage. Numerous researchers (including the Applicant herein) are working hard to try to develop "resorbable" implants, which involve matrices made of collagen fibers, polyhydroxyalkanoate polymers, or other resorbable materials. These matrices can shelter and protect certain types of specialized transplanted cells (such as chondrocyte cells, and mesenchymal stem cells) that will generate new biological cartilage over a span of weeks or months. These types of resorbable will gradually be dissolved by bodily fluids, over a span of months, in a manner similar to the gradual dissolving of collagen fibers, which are constantly being recycled and replaced in any mammalian body by new collagen fibers that are gradually secreted by certain types of cells in connective tissue.

Surgical implants that are made of collagen fibers or resorbable polymers, and that are used to nurture and protect transplanted cells that generate new biological cartilage, can also be referred to as "biological" implants, to distinguish them from non-resorbable implants made of synthetic materials. They are discussed in more detail in numerous articles and patents, including U.S. Pat. No. 6,530,956 (by Mansmann, the same Applicant herein). However, those types of resorbable implants are not discussed in any more detail herein, because they are not relevant to this current invention. Instead, this invention relates solely to non-resorbable implants that are designed to be permanent, and that will not be absorbed by the body, even after numerous years.

The types of cartilage replacement implants that are disclosed herein are designed for two distinct types of uses. One category will be anchored to hard bone structures, and will be referred to herein, for convenience, as "condylar" implants. The other category will be anchored to soft tissue rather than hard bone structures, and will be referred to herein, for convenience, as "meniscal" implants.

These two different types of implants will both require fiber-reinforced hydrogels, with smooth articulating surfaces. However, since they will require different types of anchoring structures, they are discussed under separate subheadings below.

Condylar (Bone-Anchored) Implants for Hyaline Cartilage

Most of the hyaline cartilage in any mammal covers and is anchored to the "condyles" (i.e., the rounded ends) of hard bones. In knee joints, hyaline cartilage covers the "runners" at the lower ends of femurs (thighbones), the "plateaus" on the top surfaces of tibias (shinbones), and the posterior surfaces of patellas (kneecaps). In hip joints, hyaline cartilage covers and is anchored to the rounded head (or ball) at the top of the femur, and the acetabular socket in the pelvic bone. In shoulder joints, hyaline cartilage covers and is anchored to the head (or ball) of the humerus (i.e., the large bone between the elbow and shoulder) and the glenoid socket, which is part of a scapula (shoulder blade).

Because of loadings, stresses, and other factors, the knees, hips, and shoulders are the joints that most frequently require cartilage repair. Therefore, those joints are discussed herein as the primary examples of joints where reinforced hydrogel implants can be anchored to hard bone surfaces. However, it should be recognized that these types of implants can also be used to replace cartilage in other joints where hyaline cartilage segments that cover a bone surface must be repaired or replaced; this includes fingers, wrists, ankles, and other articulating joints that have been damaged by injury or disease.

The term "condylar" implant is used herein for convenience, to refer to any reinforced hydrogel implant that will be anchored to a hard bone surface. This term distinguishes such implants from "meniscal" implants, which will be anchored to soft tissue, as described below.

Meniscal Implants (Soft Tissue Anchoring)

In addition to the hyaline cartilage that is anchored to hard bones in mammalian joints, there are several specialized segments of articulating cartilage that are anchored to "soft" tissues. Such soft tissues generally include the ligaments, tendons, and other non-bony tissues that form the "capsule" that encloses a joint. A joint "capsule" generally encloses and retains the synovial fluid that lubricates a joint.

In particular, each knee joint in a human or other large mammal contains two segments of meniscus tissue. The lateral meniscus (sometimes called an external meniscus) is located on the outer side of each knee joint, and the medial meniscus (also called an internal meniscus) is located on the inner side of the knee joint. Each meniscus has a wedged shape, somewhat comparable to a segment from an orange or other citrus fruit, but with a larger curvature or "arc" that generally resembles the letter "c". This shape is also referred to as a "semilunar" shape, since it resembles the visible moon midway between its crescent and half-moon stages.

The thickest region of a meniscus is around its periphery (also called the circumference, rim, etc.). This rim is anchored to the wall of the fibrous capsule that encloses the knee joint and holds in the synovial fluid. The two ends (also called the "arcuate tips") of each meniscal arc are coupled, via ligaments, to the bony protrusions in the center of the tibial plateau (often called the tibial spine).

The inner edge of the meniscus (i.e., the thinnest portion of the wedge) is usually called the apex, or margin. It is not anchored; instead, as a person walks or runs, the meniscal wedge is somewhat free to move, as it is squeezed between a tibial plateau (beneath it) and a femoral runner (above it). The bottom surface is relatively flat, so it will ride in a relatively stable manner on top of the tibial plateau, while the top surface is rounded, in a concave manner, so it can closely conform to the rounded convex shape of a femoral runner.

This combination of shape, location, and anchoring attachments allows each meniscus to move within a constrained area, in a manner that helps support and stabilize the outer edge of a femoral runner, as the runner rubs against the tibial plateau.

These meniscal structures also occur in the knee joints of pigs, which are present in the center of any whole ham. Anyone who is not familiar with the bone and cartilage structures described herein can inspect an actual knee joint, and can examine meniscal structures (as well as the cartilage that covers the tibial plateau, femoral runners, and patellar surface) by dissecting the knee joint that will remain after the meat has been removed from a whole ham. However, it should be recognized that the cooking process will have altered the texture and appearance of these structures.

Because human knees are subjected to frequent combinations of compression and tension (and sometimes abrasion, especially in people suffering from arthritis or other forms of cartilage damage), meniscal damage often occurs in the knees of humans, and occasionally other large animals. Therefore, various efforts have been made to provide surgical implants that can be used to replace damaged meniscal tissue. These efforts are described in patents such as U.S. Pat. No. 4,344,193 (Kenny, 1982) and U.S. Pat. No. 5,158,574 (Stone 1992), and articles such as Kobayashi et al 2003. However, because of the structural and anchoring requirements that are involved, and because of the need to create and sustain extremely smooth and constantly lubricated surfaces on both the upper and lower sides of each meniscal wedge, those prior devices are not entirely adequate.

In addition to meniscal tissue in knees, similar wedge-shaped cartilage segments that have two smooth and slippery surfaces on opposing sides also exist in shoulder joints, hip joints, and wrist joints. In the hip and shoulder joints, these specialized segments of double-surfaced cartilage are usually referred to as "labrum" tissue, since they are roughly lip-shaped (the root word labium is the Latin word for "lip"). In the wrist joint, these segments of cartilage are usually referred to as the "triangular fibro-cartilage complex", abbreviated as TFCC (the "triangular" term relates to the fact that these wedge-shaped segments have triangular cross-sections).

Because of their structural similarities to meniscal tissue (they all have two articulating surfaces, and they all are anchored to soft tissue around the rim or periphery of the wedge-shaped segment), all comments herein that relate to meniscal tissue, or meniscal implants, are also applicable to hydrogel implants that will replace labrum cartilage in hips or shoulders, or TFCC cartilage in wrists. Accordingly, the term "meniscal implants" is used herein for convenience, to refer to any wedge-shaped, meniscus-type implant that will be anchored around its peripheral rim to soft tissue (as distinct from "condylar" implants, which will be anchored to hard bone surfaces).

Despite all of the efforts cited above (and numerous others as well), surgically implantable hydrogels that are intended as permanent prosthetic replacements for injured or diseased hyaline or meniscal cartilage, in articulating joints, suffer from a number of severe limitations. As noted previously, most hydrogels contain mostly water, while the protein or polymeric strands that hold them together and give them strength usually make up only part of the volume (usually less than 10%, in most types of hydrogels in use today). This leads directly to two crucial shortcomings that have thwarted their development and use as cartilage implants. First, hydrogels developed prior to this invention do not have enough strength and durability to function successfully, in a repaired joint such as a knee or hip, for a span of numerous years, as is required for any implant that is designed to be permanent and non-resorbable. Secondly, because they are composed mainly of water, hydrogels developed prior to the Applicant's work could not be anchored to either bone or soft tissue with sufficient strength and reliability to allow them to permanently replace injured or diseased cartilage.

Those two crucial factors have severely limited and effectively blocked the successful use for hydrogels, for replacing hyaline or meniscal cartilage in articulating joints. As a result, hydrogels are used today mainly for disposable external use (such as in contact lenses, and in skin patches), or for "sustained release" drug devices, which after implantation can release a therapeutic drug for a prolonged period of time and then gradually dissolve and disappear inside the body. Because those uses do not require high strength or durability, hydrogels are well-suited for such uses.

By contrast, the goal of this invention is to disclose improved hydrogel devices, having either (and preferably both) of two enhancements that will make them stronger, more lubricious, and more durable, to a point where they can be used effectively for permanently replacing condylar or meniscal cartilage in joints, such as knees, hips, shoulders, etc.

Accordingly, this invention discloses hydrogel implants with reinforcing fiber matrices that help make the hydrogel material strong and durable enough to be implanted in a mammalian joint, as a permanent replacement for damaged cartilage.

Any use herein of terms such as matrix, mesh, fiber, fibrous, or strand, in the discussion or claims below, is intended to refer to a matrix that is made of fibers that will readily flex and bend, in a manner comparable to thread used for stitching, or strands woven into fabric. This is pointed out, because the term "fiber mesh" is sometimes used in an entirely different sense, in the field of surgical implants. Many surgical implants that are designed to be anchored to bones have rough and porous surface areas, usually made of thin strands of titanium steel or some other very hard metallic alloy. These porous surfaces are designed to promote the ingrowth of bone tissue into these implant devices. That is a highly useful process, since ingrowth of bony tissue into an implant will lead to stronger and more secure anchoring of the implant to the adjacent bone.

Despite their porosity, these types of metallic surfaces are exceptionally hard, and they are totally inflexible under any physiological pressures and temperatures. They have roughly the same feel as unpolished granite, when rubbed with a fingertip. The porous surfaces on these implants usually are created by molding and compressing strands of metal that were heated to a point where the metal alloy softened. Therefore, rippling and random patterns, formed by metallic strands that were molded and compressed while extremely hot and near-molten, can often be seen in the porous surfaces of these implants. These types of implants are often referred to as having "fiber mesh" surfaces, due to their appearance and method of manufacture. U.S. Pat. No. 5,314,478 (Oka et al 1994) offers one example of the use of "fiber mesh" to describe hardened titanium steel meshes.

However, "fiber mesh" structures made of hardened metal alloys, for promoting bony tissue ingrowth, are totally different from fibrous matrices made of flexible thread-like strands, for reinforcing flexible hydrogels as disclosed herein. As used herein, terms such as "fibrous matrix" refer to three-dimensional fibrous structures made of fibers that are readily and inherently flexible, at body temperatures. These types of fibrous matrices, and methods of manufacturing them, are discussed in more detail below, in the "Detailed Description" section.

Accordingly, one object of this invention is to disclose hydrogel implants having a combination of enhancements which will render them sufficiently strong and durable to enable effective and successful implantation and use as replacements for injured or diseased cartilage in mammalian joints. One of these enhancements involves the use of flexible fibrous matrices, embedded within at least a portion of the hydrogel material, to provide reinforcement for the hydrogel.

Another object of this invention is to disclose a composite implant having a hydrogel component, with at least one articulating layer that has been chemically treated to render it more lubricious (i.e., slipperier) and more durable, without blocking its ability to interact with water and synovial fluids in ways that emulate natural cartilage.

Another object of this invention is to disclose a surgical implant having a hydrogel component that partially encloses a three-dimensional matrix, wherein the smooth surfaces of the articulating portions of the hydrogel component are covered by a layer that has been treated by sulfonation or other suitable chemical means, to provide a more lubricious and durable articulating surface for the implant.

Another object of this invention is to disclose a composite reinforced hydrogel implant, having both (i) a reinforcing fiber matrix, and (ii) at least one articulating surface layer that has been chemically treated to render it more lubricious and durable.

Another object of this invention is to disclose a reinforced composite hydrogel implant for replacing a wedge-shaped (meniscal, labral, or TFCC) segment of cartilage, where the hydrogel contains a reinforcing matrix that: (i) is exposed on the outer peripheral rim of the implant, to enable secure anchoring of the implant to soft tissue that encloses a joint; (ii) is hidden beneath the two articulating surface layers on the inner surfaces of the wedge, which will remain completely smooth and will not abrade cartilage surfaces that rub and articulate against the implant.

Another object of this invention is to disclose a reinforced composite hydrogel implant that is designed to be anchored to a hard bone surface, wherein the implant has: (i) a porous anchoring surface, which can be permanently affixed to a hard bone surface from which cartilage has been removed, and which will promote tissue ingrowth into the anchoring portion of the implant; (ii) an articulating surface that has been chemically treated to render it more lubricious, and which has a negative charge density that emulates the negative charge on healthy cartilage; (iii) a fibrous reinforcing matrix embedded within at least a portion of the hydrogel material; and, (iv) a non-planar interface layer between the hard anchoring material and the soft hydrogel material.

Another object of this invention is to disclose a surgical implant for use in replacing a meniscal-type cartilage, having a hydrogel component that partially encloses a flexible matrix that mesh emerges from one or more surfaces of the implant, to provide improved anchoring capabilities, but wherein the mesh is not exposed on other surfaces of the implant that will articulate against cartilage segments, so that a very smooth and lubricious surface will cover the articulating surfaces of the implant.

These and other objects of the invention will become more apparent through the following summary, drawings, and description of the preferred embodiments.

SUMMARY OF THE INVENTION

A device for surgical implantation to replace damaged cartilage in an articulating joint (such as a knee, hip, shoulder, etc.) is disclosed, having at least one and preferably two reinforcing components that render the implant stronger and more durable.

One reinforcing component comprises a three-dimensional matrix made of strong but flexible fibers, embedded within at least a portion of the hydrogel material. This fibrous matrix will be covered by at least one smooth and lubricious articulating surface, and the fibers will not be exposed on that surface, since they would cause some level of abrasion if exposed at that location. In implants that are designed to replace meniscal or labral cartilage, the fibrous matrix will extend outside of the hydrogel material in a zone around the peripheral rim, to enable strong and secure anchoring of the hydrogel implant to soft tissue. In implants that are designed to be anchored to hard bone surfaces, the fibrous mesh will extend downward into a transition zone that also contains a device such as a non-planar multi-perforated interface layer, and/or a porous anchoring layer that promotes tissue ingrowth into the implant.

A second reinforcing component comprises a chemically-treated surface layer that covers at least one articulating surface of the implant, and that has been treated by sulfonation or other suitable chemical means. This chemical treatment can provide two important advantages: (i) it can render the surface layer stronger and more durable, such as by providing cross-linking bonds, halogen atoms that substitute for hydrogen protons, etc.; and, (ii) it can impart a negative charge to the implant surface, at a charge density that promotes desirable surface interactions with positively-charged components of synovial fluid.

Acting together, the reinforcing fibrous mesh and the chemically-treated surface layer can increase the strength and durability of hydrogel implants, to a level that allows them to be surgically implanted as permanent non-resorbable implants in injured or diseased joints that require cartilage repair or replacement, including high-stress joints such as knee or hip joints.

DETAILED DESCRIPTION

As briefly summarized above, hydrogel devices designed for surgical implantation to replace damaged cartilage in an articulating joint (which includes knees, hips, shoulders, etc., but which excludes the spine and spinal discs) are disclosed, having two enhancements that render the implant stronger, more lubricious, and more durable. Those two enhancements are (i) a flexible fibrous matrix, embedded in at least a portion of (and preferably throughout most of) the hydrogel material; and, (ii) at least one surface layer that has been chemically treated, such as by sulfonation, to render it more lubricious (slippery) and therefore more durable, and to give it a suitable negative charge density that will promote desired interactions with synovial fluid. By proper choice and use of chemical reagents, chemical treatment of the surface layer(s) may also render the surface layer stronger and tougher, as described in more detail below.

The implants disclosed herein can be divided into two general categories: condylar implants, which as used herein includes any implants that will be anchored directly to hard bone surfaces; and meniscal implants, which are wedge-shaped implants that will be anchored, around their peripheral rims, to soft tissue.

Figure 1:
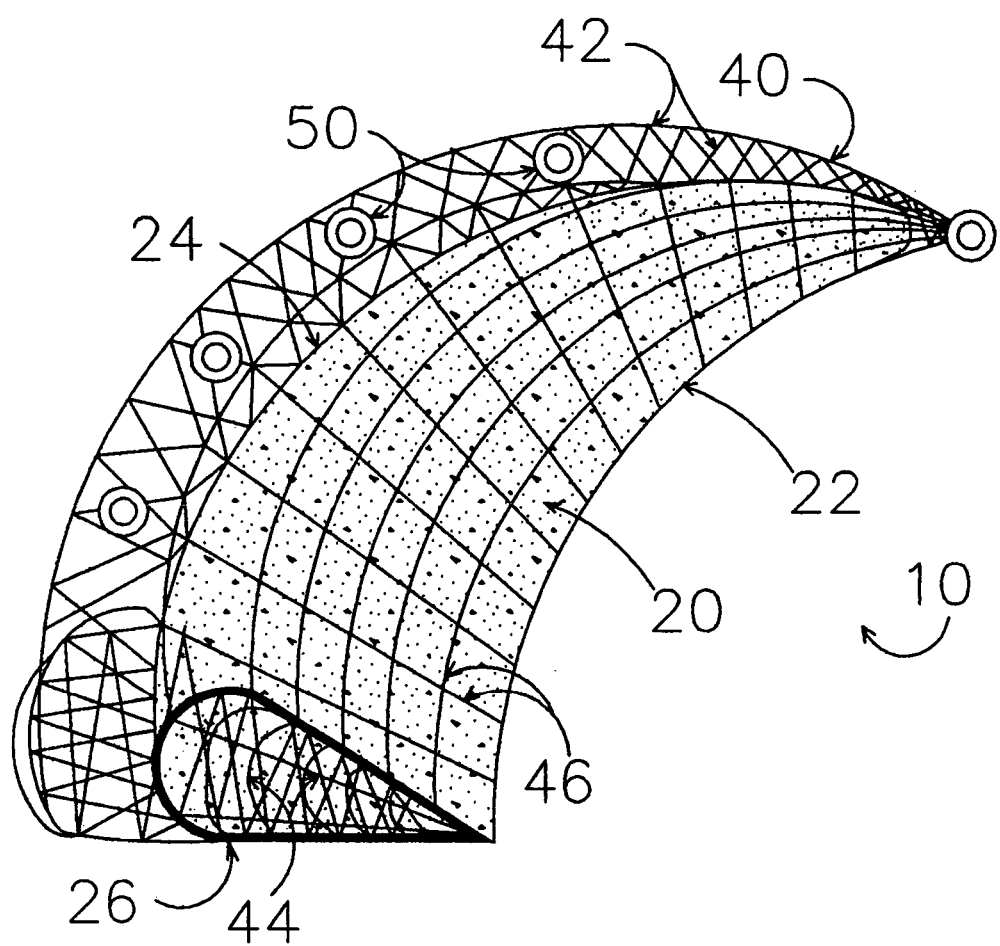
FIG. 1 is a cross-sectional perspective view of a wedge-shaped hydrogel implant, for replacing meniscal, labral, or TFCC cartilage. This implant has an embedded flexible matrix that extends outwardly from the peripheral rim, to provide anchoring support. The matrix is not exposed on the articulating surfaces of the wedge; instead, those surfaces are covered by a layer of smooth hydrogel that has been chemically treated, such as by sulfonation, to provide greater lubricity and durability.

Because meniscal implants (as shown in FIG. 1) have simpler structures and do not require specialized anchoring layers, they are discussed first, under the following subheading.

Meniscal Implants

As discussed in the Background section, each knee joint contains two meniscus segments, referred to as medial or internal (on the inner side of the knee), and lateral or external (on the inner side of the knee). These segments of cartilage are wedge-shaped, with smooth and lubricious articulating surfaces on both the upper and lower surfaces of the wedge. The peripheral rim is anchored to soft tissue that encloses the knee joint and holds in the synovial fluid.

As mentioned in the Background section, wedge-shaped cartilage segments with similar structures and anchoring attachments are also present in shoulder and hip joints, where they are referred to as "labrum" segments, and in wrist joints, where they are referred to as "triangular fibro-cartilage complex" (TFCC) segments. Because of their similarities, the discussion herein of meniscal implants is also generally applicable to (and can be easily adapted to provide) labral or TFCC implants, as will be recognized and understood by any skilled orthopedic surgeon who has repaired labral or TFCC cartilage.

FIG. 1 provides a perspective view, with a partial cut-away section, of a wedge-shaped implant 10, to replace a damaged meniscus in a knee joint. When seen from above, in a plan view, meniscal implant 10 has an arc-like crescent shape, comparable to a curved claw, with an inner surface or edge 22 (also called an apex or margin), and a peripheral rim surface 24.

Hydrogel polymer material 20 has a chemically treated surface (or "skin") layer 26, illustrated by a heavy line in FIG. 1. As described below, chemical treatment by a sulfonating or similar reagent can render surface layer 26 more lubricious ("slipperier"), and can give it a negative electrical charge density similar to the negative charge density of natural healthy cartilage. This will allow the articulating surface of the implant to interact in an improved manner with synovial fluid. In addition, chemical treatment can also render some types of polymer surfaces stronger, tougher, and more resistant to tearing and abrasion.

After implantation, the inner edge 22 of meniscal implant 10 will fit into the gap between a femoral runner (i.e., the segment of cartilage at the bottom end of a thigh bone), and a tibial plateau (the segment of cartilage at the top end of a shinbone). As in a healthy knee, the structure and placement of implant 10 will allow it to help distribute, share, and reduce the compressive loads that are imposed on the femoral and tibial cartilage segments.

Depending on the condition of a damaged or diseased knee joint, one or two single-compartment implants might be used, in either or both of the medial and/or lateral locations in the knee. Alternately, a two-compartment implant can be used, with two hydrogel compartments that are separate from each other but coupled to each other by a bundle, belt, or sheet of the mesh material that is embedded in both of the hydrogel components.

The mesh 40 shown in FIG. 1 is composed of two classes of long fibers. A number of peripheral (or anchoring) strands 42 extend out of the hydrogel material 20, around the peripheral rim 24. The peripheral rim 24 does not need to have a smooth surface, since it does not slide and articulate against a cartilage surface.

By contrast, "embedded" strands 44 of the flexible matrix pass through the hydrogel material 20. Due to the woven, knitted, or other three-dimensional structure of the mesh, a single long strand in matrix 40 might provide a peripheral/anchoring strand 42 at one location and an embedded strand 44 at another location.

FIG. 1 also illustrates five anchoring reinforcements 50, located around the periphery of the mesh 40. In one preferred embodiment, these can be made of the same stranded material that makes the mesh, in a manner comparable to sewing or weaving a buttonhole using the same type of thread that is used to sew a garment together. Alternately, these can be made of a molded or machined material, such as a biocompatible plastic or metal. Since anchoring reinforcements 50 will be positioned away from any articulating cartilage surfaces, they can be designed for strength, and do not have to be perfectly flat or smooth.

In the discussion herein, it is assumed that the mesh 40 extends outside of the hydrogel polymer 20, around the peripheral rim 24. However, alternate designs can be tested and used, if hydrogel implants having protruding fibers suffer from damage to the hydrogel polymer, around the periphery. As one example, a series of reinforced eyelets can be embedded inside the hydrogel polymer, by attaching the eyelets to fibrous mesh which is embedded within the gel material. If this design is used, suture material can be passed through the hydrogel and through the eyelets, by the surgeon doing the operation. As another example, a tough elastomeric material made of an entirely synthetic polymer (which will not be classified as a hydrogel, if the polymeric material does not hold and retain water molecules) can be used to provide the peripheral rim surface of a meniscal implant, from which the reinforcing fibers will emerge.

Regardless of whether the mesh component extends beyond the peripheral rim of an implant, the peripheral rim of a meniscal implant can be provided with a porous outer layer, to promote tissue ingrowth into the porous rim region of the implant. This type of porous layer can be created in a hydrogel or elastomeric polymer by steps such as using a layer of salt, sugar, or other granular compound (or "intercalating" fibers or other material, such as a wax-like material that can be melted and/or vaporized at a temperature that will not damage the gel or elastomer), during the processing step that is used to mold the gel or elastomer in the rim area. Alternately, methods comparable to surface etching, using acids or other chemicals, laser beams or other types of radiation, etc., may be useful, depending on the type of hydrogel or elastomeric material being treated.

In FIG. 1, fibrous strands 46 are visible in the perspective view portion of the drawing, because the thin layer of hydrogel material that covers fibrous strands 46 is essentially clear and transparent, due to its high water content. However, those fibers preferably should not be exposed on either of the upper or lower articulating surfaces of implant 10, because their presence on an articulating surface would generate elevated risks of roughness and abrasion, especially over a span of time measured in years. Accordingly, strands 46 should be regarded as being for illustration only, to indicate that in this particular embodiment, the mesh extends through essentially the entire hydrogel component, other than the sulfonated surface layer 26.

In most types of non-resorbable cartilage-replacing implants, as a general design principle and unless some particular factor requires or indicates otherwise, the reinforcing fibrous mesh normally should extend through as much of the hydrogel material as possible, consistent with preventing its presence on an articulating surface (where exposed fibers might create or aggravate a rough and abrasive surface). This is especially true in implants that will be subjected to relatively high stresses, as occur in knee and hip joints.

However, depending on various factors (including (i) the age, weight, and physical condition of a patient; (ii) which particular joint is being repaired; and, (iii) the strength and toughness of the polymeric material that is being used to form the hydrogel), it may not be essential to ensure that a reinforcing mesh extends throughout essentially all of an implant other than a shallow surface layer. For example, if an implant is being used to replace a cartilage segment in a finger or wrist, where loading stresses are relatively low, it likely will be sufficient to use only a relatively small region of reinforcing mesh, or perhaps even to eliminate the reinforcing mesh altogether, if a sufficiently tough and durable surface layer is provided by crosslinking or other chemical treatment, as discussed below. Accordingly, some claims below relate to hydrogel implants with chemically-treated surface layers, regardless of whether they also have a flexible fibrous matrix embedded in the hydrogel material. Similarly, some claims relate to hydrogel implants that have a reinforcing fibrous matrix embedded in at least a portion of the hydrogel material, regardless of how large that portion is, in some types of implants.

Despite the foregoing, any implant generally should be designed to last as long as possible, regardless of what kinds of loading stresses it might be subjected to in a recipient, and any design of such implants must take into account the risk of falls or other accidents that may cause high instantaneous loadings. Therefore, it is preferable for a reinforcing mesh to extend throughout the large majority (and, where possible, essentially all) of the hydrogel material in such an implant, except for a relatively shallow surface layer (where the need to provide retain the highest possible level of smoothness usually will override a desire for additional reinforcement).

As mentioned in the Background section, the two ends (or "arcuate tips") of each meniscus have ligaments extending therefrom. These ligaments essentially are wrapped around the internal rounded surfaces of a femoral runner, and the ends of the ligaments are affixed to the hard bony protrusions that form the "spine" in the center of the tibial plateau.

To provide these additional anchoring sites for a meniscal implant, the fibrous reinforcing matrix in a meniscal implant can be manufactured in a way that causes a bundle of fibers to extend out of the ends (the arcuate tips) of the implant. This can allow the protruding fiber bundle to be sutured or otherwise coupled to the ends of natural meniscal ligaments, which can remain attached to the spinal protrusions in the center of the tibial plateau. Alternately, if the natural meniscal ligaments cannot be used and must be removed, the ends of the fiber bundles can be attached directly to the tibial spine protrusions, or to the head of an anchoring pin or other device that has been driven into the tibial bone.

Labrums tend to have more variability, between different patients, in their attachments to bones and ligaments, when compared to meniscal segments in knees, and TFCC segments in wrists have still greater levels of variability, in many patients. Nevertheless, those variations are fully known to skilled orthopedic surgeons, and those surgeons can readily adapt reinforced and surface-treated wedge-shaped implants, as disclosed herein, for implantation into hip, shoulder, or wrist joints, using methods known to those skilled in that art.

Condylar (Bone-Anchored) Implants

As described in the Background section, the term "condylar implant" is used herein to refer to a hydrogel implant that will be anchored to a hard bone surface.

Although the smooth articulating surfaces will be essentially the same, in both condylar and meniscal implants (i.e., with a chemically-treated surface layer, and an underlying reinforcing mesh), condylar implants will be different from meniscal implants, because of the requirements that arise in anchoring condylar implants to hard bone surfaces. Whereas meniscal implants provide wedge-shaped hydrogel segments, with two distinct articulating surfaces and a peripheral rim that will be anchored to soft tissue, condylar implants have only one articulating surface, and the opposite side must be anchored permanently and directly to a hard bone surface. That bone surface will need to be prepared, usually by removing any remaining cartilage from it; usually, this can be done during the same surgery that will be used to emplace and anchor the implant.

Figure 2:
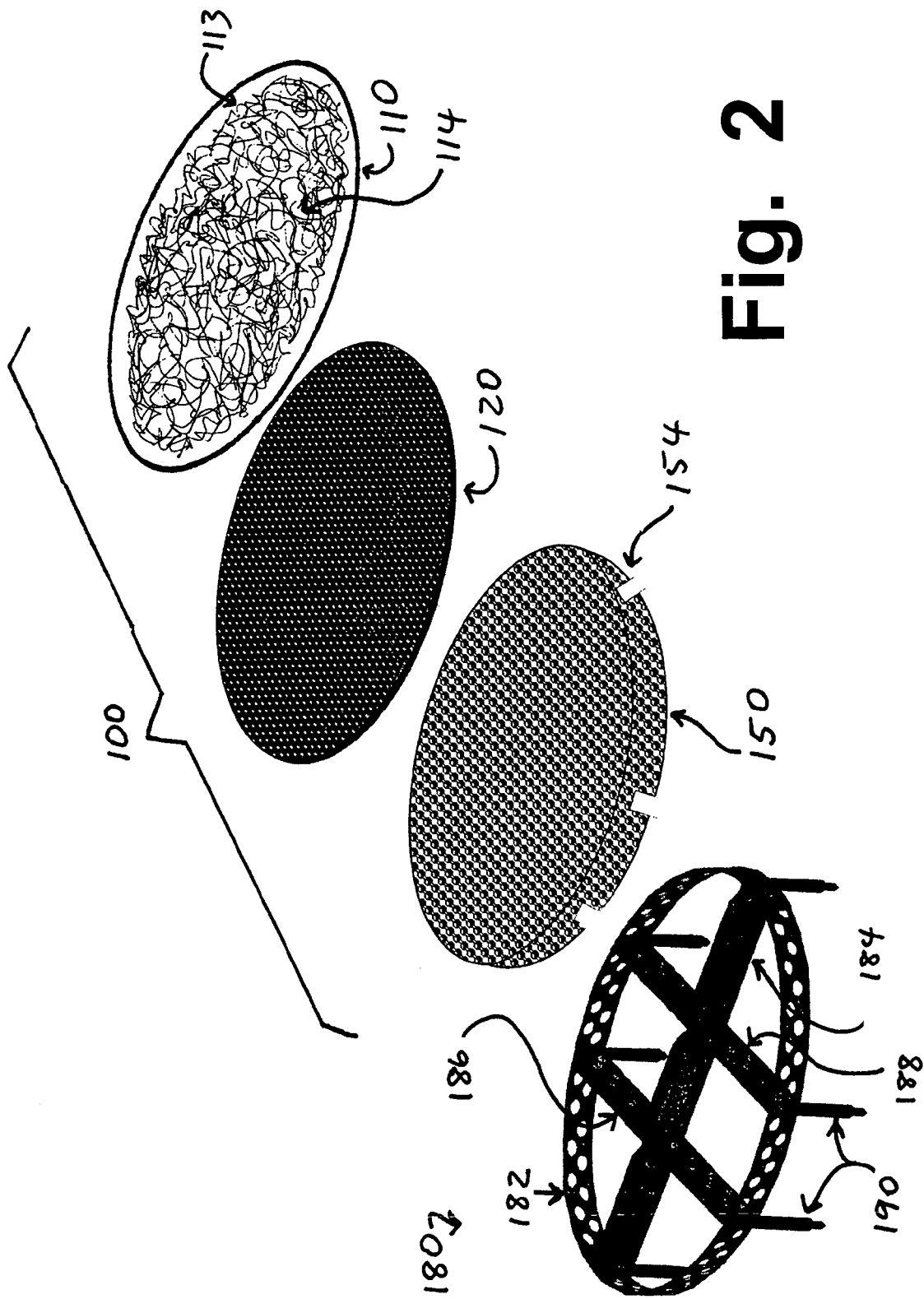
FIG. 2 depicts a condylar-type implant that will be anchored to a hard bone surface, showing a hydrogel layer, a non-planar multi-perforated interface layer, and an anchoring layer that will promote tissue ingrowth. This implant is adapted for use with an anchoring grid, also shown, which has pins that will be set into hard bone.

The structure of one preferred embodiment of a condylar implant is illustrated in FIG. 2, and is discussed in more detail in U.S. patent application Ser. No. 10/071,930, filed in February 2002 by the same Applicant herein. The contents of that application are incorporated herein by reference, as though fully set forth herein.

Briefly, the components or layers shown in FIG. 2 comprise a condylar implant 100 having three main layers, which are a hydrogel surface (articulating) layer 110, a non-planar interface layer 120, and a bone anchoring layer 150. When fully assembled, these three layers can be regarded as a unit, subassembly, etc.

If desired, implant 100 can be secured to an anchoring grid 180 (as illustrated in FIG. 2) or to some other type of anchoring structure (such as an anchoring layer that can contain female-type sockets or "receptacles" that can hold and secure male-type pins on the bottom of a hydrogel implant. This approach can be used to securely affix a soft-surface hydrogel implant to a prepared bone surface during a surgical procedure, in a manner than minimizes any handling of the hydrogel material, and that minimizes any risk of abrasion of, distortion of, or other damage to, the hydrogel implant or its soft surface. Alternately, if preferred, pins, cement, and/or other suitable means can be used to secure a bone anchoring layer 150 of an implant directly to a prepared bone surface, without requiring an additional anchoring grid or other component.

Implants 100 can be made in various sizes and shapes (such as large, medium, and small versions of femoral runners, tibial plateaus, etc.), and they can be stored and shipped in sealed packages that will maintain sterility, in either hydrated or dehydrated form. At an appropriate time, which in most cases will be during or shortly after a diagnostic procedure, or during the surgery itself), a surgeon can select an implant having the preferred size and shape for a particular patient.

In FIG. 2, components 110-150 are shown in a relatively flat and planar form, for simplicity of illustration. However, any such implant should be designed and manufactured in a way that will allow it to rest, securely and with minimal stresses, on top of the prepared bone surface where it will be anchored. As examples, an implant for replacing cartilage on a tibial plateau normally will have a relatively flat and planar anchoring surface, while an implant for replacing a femoral runner preferably should have a curved or faceted anchoring surface.

Hydrogel layer 110 will provide the smooth and slippery (or "lubricious") articulating ("bearing") surface of condylar implant 100. In the same manner described above for meniscal implants, hydrogel polymer 110 should be provided with a sulfonated or otherwise chemically-treated surface layer 112, to make it more lubricious (i.e., slipperier) and more durable.

As described below, under the heading "Chemical Treating of Surface Layers," surface treatments using selected chemicals can also render at least some types of synthetic polymer surfaces stronger, tougher, and more resistant to tearing or abrasion.

Because of the highly porous nature of a hydrogel (which is formed by a porous matrix that must provide large quantities of unoccupied internal volume, which water molecules will occupy in the fully-hydrated hydrogel), it is presumed that in most hydrogel polymers, the surface layer that will be affected by the sulfonation or other chemical treatment will is likely to extend to at least some shallow or moderate depth, beneath the actual surface. Accordingly, in FIGS. 2 and 3, callout number 112 refers to the entire thickness of the surface and near-surface layers that will be chemically altered by sulfonation or other chemical treatment, and callout number 113 is used to refer to the outermost membrane that forms the articulating surface of implant 100.

It is also presumed that the boundary between the chemically altered surface layer 112, and the underlying supporting layer, will not be a completely flat boundary, with no thickness. Instead, because of the highly porous nature of the hydrogel, this boundary will be a transition zone, with fully sulfonated polymer on one side of the transition zone, and unsulfonated polymer on the other side. This is implied by the dotted-line boundary, shown as the lower edge of the chemically altered surface layer 112, in FIG. 3.

Beneath the outermost surface membrane 113, a three-dimensional fibrous mesh or matrix 114 (depicted in simplified form in FIG. 3) is embedded within the hydrogel polymer. Preferably, this fibrous matrix should not be exposed on the outermost surface membrane 113, since any exposed fiber strands likely would create or aggravate problems of roughness and abrasion, over a span of years.

Preferably, the fibrous matrix 114 should be laced around or connected to, or should penetrate through or otherwise be coupled to, the interface layer 120, which generally should be made of a relatively stiff and hard layer of plastic, metal, or other suitable material. Interface layer 120 (a portion of which is shown in greater detail in FIG. 4) is designed to create a non-planar, distributed interface or transition zone between the hard material in bone anchoring layer 150, and the much softer hydrogel material in layer 110. If a hydrogel material is coated onto a hard material by means of a simple flat planar interface, shear forces that are exerted on the implant will tend to be focused on that planar interface, and the implant is more likely to be damaged and destroyed by tearing, over a span of months or years. By contrast, the shape and structure of interface layer 120 is designed to allocate and distribute fluid pressures across a variety of surfaces, and in a variety of different directions. This will effectively create a thicker, better-distributed, and more adaptable and stronger transition zone, between a hard anchoring material and a soft hydrogel material.

Figure 4:
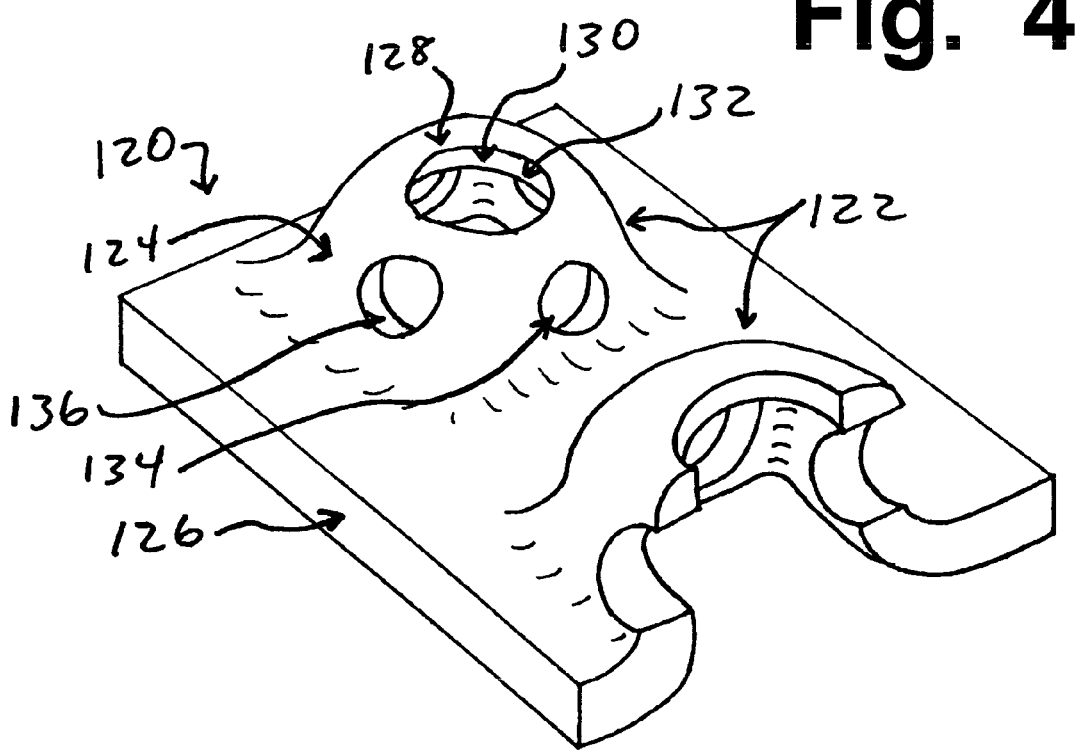
FIG. 4 is a perspective cutaway view of a small segment of a non-planar multi-perforated interface layer. This interface layer can distribute fluid pressures across a transition zone, in a condylar implant, to create a stronger interface between the hard anchoring material and the soft hydrogel material.

A small segment of interface layer 120 is shown in a perspective cutaway view, in FIG. 4. This cutaway drawing depicts two of the numerous "riser bumps" 122 in layer 120. These riser bumps will be arrayed in a geometric pattern in layer 120. Suitable geometric patterns can include rectangular, diamond, hexagonal (honeycomb), or any other suitable pattern.

Each riser bump 122 in layer 120 has one or more semi-vertical sides or facets 124, rising out of a "grid" layer 126, which will rest on top of the bone anchoring layer 150. Any directional terms used herein (vertical, horizontal, above, below, etc.) with regard to the interface 120 assume that the grid layer 126 is horizontal and the riser bumps 122 extend upward, as depicted in FIGS. 2 and 4.

The uppermost surface 128 of each riser bump 122 is referred to herein as a horizontal facet. It preferably should be relatively flat, rounded, and smooth, and the semi-vertical facets 124 also preferably should be provided with rounded corners, if any corners are present. The absence of any sharp corners can reduce any risk of internal cutting, abrasion, or similar damage, if a patient with an implant falls, must jump down from an elevated height, or suffers some other accident or event that would cause a knee, hip, or other joint to suffer an instantaneous peak compression or other loading during impact.

As shown in FIG. 4, each roughly vertical facet 124, and each horizontal facet 128, has a plurality of holes 130 (which can also be called a perforation, orifice, aperture, etc.) passing through it. If desired, these holes 130 can be categorized as horizontal holes 132, longitudinal holes 134 (which assumes that the implant has its longest dimension in the direction from upper left to lower right, in the drawing), and transverse holes 136.

Acting together, riser bumps 122 and the numerous perforations 132-136 which pass through the riser bumps create a complex non-planar multi-perforated outer surface, in interface layer 120. In addition, as can be seen from the visible portions of the "underside" surfaces 138 shown in FIG. 4, the outer-surface facets 124 and 128 are also supplemented by still more surfaces or facets, on the underside of the interface layer 120. All of those surfaces or facets are exposed and accessible to the water molecules in a hydrogel. Therefore, all of those surfaces or facets can resist fluid pressures that are imposed on those facets. In this manner, the complex surface geometry of interface layer 120 can allow the interface layer to use fluid flow and fluid pressures, within a hydrogel, to redistribute and disseminate the compressive and/or shear forces that are imposed on the articulating surface 112 of flexible implant 100 as shown in FIGS. 2 and 3.

Figure 3:
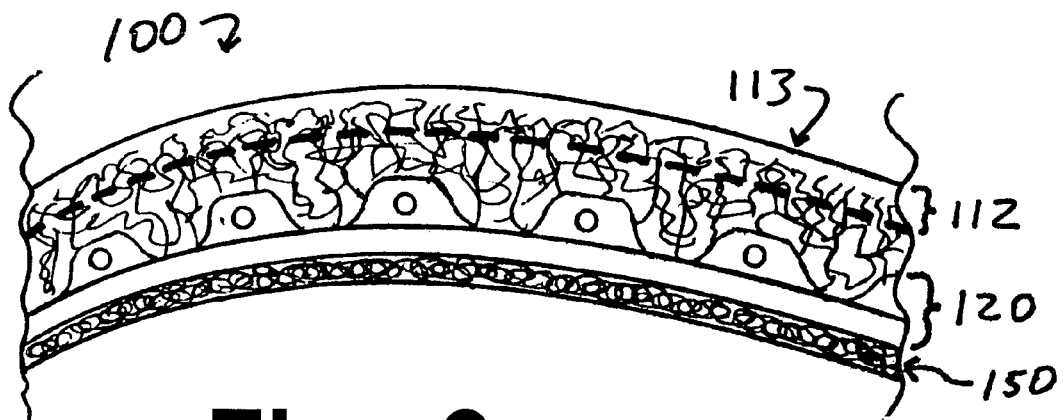
FIG. 3 is a cross-sectional view of a condylar-type implant, designed to be anchored to a hard bone surface. The primary layers or zones of this implant include: (1) a smooth articulating surface made of a hydrophilic polymer, having a "skin" surface that has been chemically treated to provide higher strength and durability, and better interactions with synovial fluids; (2) a flexible reinforcing matrix, beneath the treated "skin" surface of the implant; (3) a non-planar multi-perforated interface layer, to help distribute and strengthen the interface between the relatively soft hydrogel material and the much harder anchoring layer; and, (4) an anchoring layer, comprising a hard metallic mesh and/or porous ceramic that will promote tissue ingrowth.

Bone anchoring layer 150, shown in FIGS. 2 and 3, provides the porous bottom surface 152 that will directly contact a prepared bone surface and promote ingrowth of bony (osseous) tissue. It can be made of a stiff and rigid material, such as a porous ceramic or a mesh made of compressed strands of titanium steel or other very hard alloy.

Alternately, bone anchoring layer 150 (which can be relatively thin) may be made of a metallic mesh or other material that will allow a substantial degree of flexure, so that the entire condylar implant 100 can be flexed or "curled" somewhat, to allow it to be inserted into a joint through a smaller surgical or arthroscopic incision, to minimize damage and disruption to the surrounding tissue and vasculature.

In either embodiment, a metallic alloy or other substrate material used to make layer 150 can be sputter-coated with a layer of a calcium-phosphate mixture, to emulate the hydroxyapatite crystals in bone. This may help promote greater or more rapid entry of bone-forming cells into the anchoring layer 150.

The rim of anchoring layer 150 is shown as having three "gaps" 154. If the implant is affixed to an anchoring grid 180, as discussed below, gaps 154 will align with the internal runners 184-188 of the grid 180, to allow a more secure fit.

Interface layer 120 can be bonded, fused, or otherwise secured to the anchoring layer 150 by any suitable method (such as chemical bonding of a polymeric interface to a ceramic or metal anchoring layer, use of welding or brazing if both layers are made of metal, etc.). Alternately, it may be possible to fabricate both layers from a single type of material, such as by a combination of techniques that might include, for example: (i) molding a polymeric compound in a mold which is partially occupied, in the bottom layer, by a granular compound (such as salt, sugar, etc.) that can subsequently be dissolved by water or a suitable solvent; (ii) dissolving and removing the granules, thereby creating a porous structure on the bottom layer which promotes cell ingrowth; and, (iii) machining the top layer by means of laser beams, small drill bits, or other suitable means, to create the multiple non-planar perforations on the riser bumps.

Anchoring grid 180, shown in FIG. 2, is optional. It comprises a rim structure 182, which will be held in position on a bone surface by pins 190. Pins 190 can pass through accommodating holes in the rim 182, or if desired, they can be coupled to rim 182 via hinges or similar methods, so that the entire device can be folded into a flattened configuration during surgical insertion. Depending on the size of the implant, the anchoring grid 180 may have one or more internal longitudinal "runners" 184, and one or more transverse runners 186 and 188.

Alternately, if an anchoring grid is not used, pins and/or other devices can be used to attach the bone anchoring layer 150 directly to a prepared bone surface.

As mentioned above, a prior version of this type of condylar implant is also discussed in U.S. patent application Ser. No. 10/071,930, by the same Applicant herein. However, two new and different structures in the improved condylar implant 100 of this invention distinguish the improved version from the prior disclosed version:

a three-dimensional fibrous matrix 114, which is embedded within at least a portion of the hydrogel polymer that forms bearing layer 110, but which does not appear on the smooth bearing surface 113 of implant 100. This reinforcing mesh preferably should be coupled to at least some portion of the interface layer 120, for additional strength. This coupling can be done by chemical means, mechanical weaving or interlacing, or any other suitable means.

(ii) a chemically-treated surface layer 304, created by sulfonation or other suitable chemical treatment, as discussed in more detail below.

Manufacturing of Fibrous Meshes

As mentioned in the Background section, terms used herein such as matrix, mesh, fiber, fibrous, or strand, refer to a matrix that is made of fibers that will readily flex and bend, at body temperature, in a manner comparable to conventional thread used for stitching. These types of fibrous matrices exclude the types of so-called "fiber meshes" made of titanium steel or other hard materials that are used to provide hard but porous anchoring layers that will promote bony tissue ingrowth, in an implant.

For maximum strength, matrices that are more complex and intertwined than simple "warp and woof" structures are preferred, and can be created by various known processes. One such process, involving computer-controlled three-dimensional weaving, has been developed by a company called Techniweave (Rochester, N.H.; its Internet address is www-.techniweave.com). It is a subsidiary of Albany International, a producer of machinery for processing paper and other materials.

Another process that may be useful for creating fiber matrices for reinforcing hydrogels is called "needle-punching". This process has been used for years to make insulated padding layers that are placed beneath carpets in high-traffic sites, such as stores, theaters, offices, etc. As described in PCT application PCT/US01/11895, published as WO 01/76869 (Bacon et al), these types of large needle-punched pads are now being treated with adhesives, to allow recycled carpet to be converted into strong and waterproof substitutes for sheetwood materials such as plywood.

To manufacture a needle-punched fiber mat for use as a carpet underlayer, a thick and fluffy layer of fibers is laid on top of a large and wide conveyor, by using a series of "cross-lapper" machines. These devices travel back and forth, on rails, over a slow-moving conveyor which is usually made of parallel slats, laying down wide ribbons of combed fibers on top of the conveyor. After the cross-lapping operation is complete (this typically requires four cross-lapper machines, in series, the fluffy layer (which is more than a foot thick) is compressed between rollers, to form a mat that is roughly half an inch thick.

This mat is then passed through a needle-punch machine. This machine has a large plate (usually called a platen), which spans the entire width of the conveyor system, and which reciprocates vertically, usually at about 5 cycles per second. This platen has numerous needles extending downwardly; roughly 10,000 needles are used in a machine that makes carpet padding rolls 12 feet wide, which is standard for the carpet industry. Each needle has about 12 to 20 small nicks or barbs, at spaced locations along a portion of its shaft. These barbs will grab individual nylon fibers, and will yank them both upward and downward, as the fiber mat passes through the needle-punch machine.

By adjusting various factors (including the number and spacing of needles in the platen, the reciprocating speed of the platen, and the "dwell time" of the mat as it passes through the needle-punching zone), needle-punching can generate a mat that will have a three-dimensional interlaced structure that causes it to hold together strongly, without requiring any expensive chemical adhesives.

These materials have remarkably good wear properties. Even if the overlying carpets must be replaced every three to five years in a high-traffic area, the padding layer usually can last for 15 to 25 years, with essentially no flattening. Alternately, if chemical adhesives are added, to convert a flexible mat into a stiff plywood substitute, the resulting materials can have extraordinary strength and mechanical properties, due to both (i) the highly interwoven structure of the fiber matrix, and (ii) the ability of certain adhesives to bind very strongly to nylon fibers.

For similar reasons, needle-punched fiber mats (which obviously would be much smaller, thinner, and less dense than mats made for carpet pads), may be very well suited for use in creating reinforced hydrogels.

Other types of three-dimensional fibrous matrices, created by means such as chemical crosslinking of fibrous strands with each other, can also be evaluated for use as disclosed herein, if desired.

Chemical Treatment of Polymer Surfaces

During his research on several types of candidate polymeric materials that can be used to make hydrogels, the Applicant has tested poly(vinyl alcohol), abbreviated as PVA; copolymers containing units of PVA interspersed with small quantities (such as 1%) of poly(vinyl pyrrolidone), abbreviated as PVA/PVP; and polyacrylonitrile, abbreviated as PAN.

While testing various candidate preparations for potential use in cartilage implants as disclosed herein, the Applicant discovered that all of them can be given surface layers that are substantially more slippery (and therefore better-suited and more durable, if used to form the surfaces of cartilage implants), if they are treated by a sulfur-donating reagent, such as diluted sulfuric acid. Layman's term such as "more slippery" are used interchangeably herein with more scientific terms such as "greater lubricity" or "more lubricious".

The process of adding sulfur atoms to other molecules (such as hydrogel polymers) is referred to herein as sulfonation. When using a synthetic polymer that will form a hydrogel, it can be carried out by submerging the polymer material in a bath of diluted sulfuric acid for a relatively brief period of time, at a suitable temperature. Alternately, sulfonation can be carried out by using other sulfur-containing reagents, such as sodium sulfite, sodium bisulfate, sulfur trioxide or dioxide, a mixture called oleum ($SO_3$ dissolved in sulfuric acid), etc., using solvents and reaction conditions that are known to those skilled in sulfonation chemistry (see, e.g., E. E. Gilbert, *Sulfonation and Related Reactions* (Interscience Publishers, New York, 1965)). Recipes for creating sulfonated surface layers on PVA hydrogels, and on PAN hydrogels, are provided in the Examples below.

Unless steps are taken to deliberately generate sulfate groups that are double-bonded to a hydrogel polymer, sulfonation of hydrogel polymers using reagents such as sulfuric acid will normally generate sulfate groups (i.e., a sulfur group that contains at least one oxygen atom) that are bonded to a carbon or nitrogen atom in the polymer, by means of a single bond. Since sulfuric acid ($H_2SO_4$) contains a sulfur atom that is surrounded by four oxygen atoms, the bond that is created when sulfuric acid is used normally will be an ester-type bond (i.e., with one oxygen atom positioned between the sulfur atom and the nitrogen or carbon atom of the polymer, and with at least one oxygen atom double-bonded to the sulfur atom), unless steps are taken to create a different type of bond between the sulfate group and the polymer.

However, if other types of sulfonating agents (such as sulfur dioxide, sodium sulfite, etc.) are used, the opportunity arises (with at least some types of polymers) to create either or both of two other types of bonding structures: (1) direct bonds, in which a sulfur atom is bonded directly to a nitrogen or carbon atom of the polymer; and/or, (2) crosslinking bonds, in which a sulfur atom forms a bridge (or at least a part of a bridge, as occurs in disulfide bonds) between two carbon atoms, polymer strands, or other molecular structures. Both of these approaches to creating sulfonated hydrogel surfaces with direct and/or crosslinking bonds deserve evaluation, as research progresses on this and related inventions, because either or both of those approaches may be able to impart greater strength, toughness, and durability to a hydrogel surface. Crosslinking reactions in particular are often used to give greater strength and durability to various types of membranes (including, as just one example, in the use of tannin and other crosslinking chemicals to process animal skins into strong and durable leather).

If desired, other electronegative surface-treating agents can also be evaluated for use as disclosed herein. In particular, reagents (or prepolymeric compounds) that substitute halogen atoms for hydrogen protons, in a polymeric material, can be evaluated for use as described herein. The bonds between hydrogen protons and carbon atoms in a polymer are not especially strong, and replacement of hydrogen by other compounds can often lead to stronger and more durable polymers. Examples of this process are described in patents such as U.S. Pat. Nos. 4,621,107 and 4,900,793 (both by Lagow et al), which disclose "perfluorinated" elastomers, in which substantially all of the hydrogen atoms in an elastomeric polymer are displaced by fluorine atoms. Accordingly, fluorinating agents (and possibly other halogenating agents), and prepolymeric compounds that already contain halogen atoms instead of hydrogen protons in at least some locations, can be evaluated for use as described herein, if desired.

Alternately or additionally, chemical agents that can donate non-sulfurous bi-valent or multi-valent electronegative atoms (such as phosphorus) to a treated polymeric surface can also be evaluated for use as disclosed herein, to impart negative charges to the polymer surface, and/or to provide higher strength (due to crosslinking or other cause) to the polymeric surface.

Synovial Macromolecules; Lubricin/SAPL Complexes

The following section, which accompanies and offers a narrative for FIG. 5, is offered as a model, or theory, to help explain how sulfonation substantially improves the interactions between a polymeric surface membrane, and certain components of synovial fluid. This model and theory is simplified, and is not intended to be exhaustive or comprehensive, and the invention disclosed herein does not depend for its validity on the accuracy of this model. Instead, this depiction is offered merely as part of an effort to help readers understand a putative mechanism that may help clarify and explain a set of complex interactions between natural biological fluids, and specially-treated synthetic polymers.

In addition to water and various nutrient and "building block" molecules (such as glucosamine, chondroitin, etc.) that are used to make cartilage, the molecules that make synovial fluid much more slippery and viscous than water include two classes of large "macromolecules":

(i) hyaluronic acid (HA), which exists mainly in ionized form, called hyaluronate. A molecule of HA or hyaluronate normally is formed by stringing together large numbers of alternating rings of glucosamine, and glucuronate (the ionized form of glucuronic acid). In synovial fluid, the molecular weight of HA/hyaluronate usually ranges from about 50,000 up to about 8 million daltons; and, (ii) two compounds called "lubricin" and "surface-active phospholipid" (SAPL). These two types of molecules alternate back and forth between free (unassociated) forms, and "complexes" that are held together by inter-molecular attraction, rather than by covalent bonding. These complexes are assumed to form under resting conditions, inside a stationary joint, when no compressive or shear forces are being exerted on the joint, or on the macromolecules in the synovial fluid that fills the gap between two adjacent cartilage surfaces.

When a knee or other joint is flexed and moved (especially when it is moved while under compression, as occurs in a knee joint when a person is walking), in a manner that causes two segments of cartilage to slide against each other while being pressed together, the lubricin/SAPL complexes can be pulled apart, without damaging either component, in a manner comparable to pulling apart two relatively weak magnets. The separated components will eventually recombine (presumably after the activity ends and the joint returns to a resting state), thereby reforming new lubricin/SAPL complexes, which will be ready to participate again, in the same manner, when the next activity commences.

This process, which involves forming, separating, and reforming lubricin/SAPL complexes as part of a larger and more complex process, is illustrated, in simplified form, in FIGS. 5A through 5E.

Figure 5A:
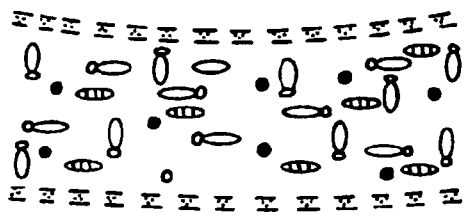
FIG. 5 is a multi-part figure depicting the interactions between synovial fluids and cartilage surfaces, during various stages of resting, compression, and articulation, inside a knee joint.

FIG. 5A, labelled "Unloaded Joint Space", is a cross-sectional depiction of a small portion of a knee joint that is relaxed, resting, and not under pressure. The top and bottom "semi-permeable" membranes shown in FIGS. 5A through 5E represent only the outermost membranes that cover the opposing surfaces of two segments of cartilage. In each part of FIG. 5, the upper membrane is part of a femoral runner, while the lower membrane is part of a tibial plateau.

As indicated in FIG. 5A-E, these two membranes do not contact each other. Instead, the gap between them is filled with synovial fluid, which contains hyaluronate molecules, lubricin/SAPL complexes, and other smaller molecules such as glucosamine, chondroitin, etc., all suspended in water.

The membranes that form the surfaces of the femoral and tibial cartilage segments are "selectively permeable". In general, each cartilage membrane is composed of a thin layer, made up mainly of interconnected collagen fibers. As mentioned in the Background section, collagen is a fibrous protein; it forms the matrix that holds cells together in nearly all types of cohesive flexible tissue, including muscle, skin, organs, etc. Each thin membrane made of interconnected collagen fibers allows water molecules to flow through it in a rate-controlled manner; as discussed below, this allows fluid loads and pressures to be redistributed across the membrane in a regulated manner as the joint is "loaded" with weight.

Each collagen membrane also allows some but not all of the "macromolecules" which lubricate the joint to permeate through that membrane. The massive hyaluronate molecules are assumed to not penetrate through or permeate into the surface membranes at all, while the smaller building blocks of cartilage (such as glucosamine and chondroitin) can gradually permeate through the membranes, allowing them to reach the cartilage beneath the membranes.

The relationship between the membrane and lubricin/SAPL complexes is not yet fully understood; however, for purposes of the simplified model described herein, it is assumed that lubricin molecules can at least partially penetrate into that membrane, while SAPL molecules do not penetrate or enter the membrane at all (at least, not in substantial quantities).

Figure 5B:
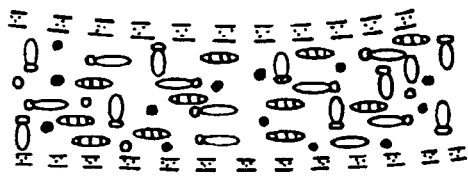

FIG. 5B (labelled "Instantaneous Loading") illustrates what happens when the joint is initially compressed after being at rest, such as when the person stands up. As the person goes through the motion of standing, the bottom surface of the femoral runner begins to slide toward the rear, on the tibial plateau. As this type of sliding motion occurs, pressure is imposed on the joint, due to the weight of the person.

During this initial sliding and loading motion, within the zone of highest pressure within the joint, the cartilage surfaces on the femur and tibia initially engage in a "hydroplaning" motion. As this is occurring, the macromolecules in the synovial fluid are being compressed, as shown by their slightly greater density in FIG. 5B compared to the fluid in the relaxed joint of FIG. 5A. However, lubricin molecules have not yet had time to begin permeating into either of the cartilage membranes, and the much smaller water molecules have had only an instant to commence that process. The two cartilage membranes do not contact each other during this "hydroplaning" stage; instead, the femoral runner is kept suspended above the tibial plateau by the synovial fluid that fills the gap between them.

Figure 5C:
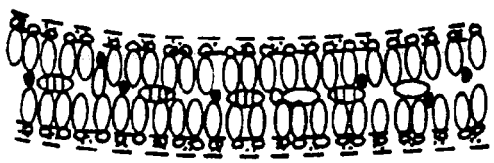

FIG. 5C ("Static Compression") schematically illustrates the condition that will arise within the zone of maximum compression inside the joint, if the person remains standing still for several minutes. Under sustained static pressure, the lubricin/SAPL complexes are forced to seek an arrangement that minimizes their volume, and they begin to line up in an aligned configuration as shown. The lubricin "heads" will, to at least some extent, contribute to this alignment between the cartilage membranes; although this process is not fully understood, it is assumed herein, for purposes of discussion and illustration, that the lubricin "heads" will fit into the interstitial spaces between adjacent collagen fibers in the membrane surfaces of the two cartilage segments, and the SAPL "tails" will project away from each cartilage membrane, into the synovial fluid.

In addition, this type of static compression is also assumed to drive at least some water molecules (which are much smaller and more mobile) out of the high-pressure zone, thereby increasing the relative concentration of the much larger and less mobile lubricant molecules in that zone. This will increase the thickness and viscosity of the lubricant fluid that remains.

Figure 5D:
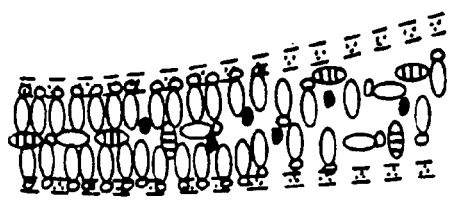

FIG. 5D ("Hydroplaning Motion") illustrates what happens if the person then begins walking forward, after standing still for a sustained period. Shear forces exerted on the synovial fluid by the relative motion of the two membranes cause the SAPL/lubricin concentrate in the contact zone to lubricate the initial launch of the joint into a hydroplaning mode of load transfer. As mentioned above, this action and the shear forces that are generated by this action are believed to cause at least some lubricin/SAPL complexes to be pulled apart.

These various actions (including dissociation of lubricin/SAPL complexes, mixing of the SAPL molecules with hyaluronate, and the mobile departure of water and other small solute molecules from the highest-pressure zone) lead to formation of a highly viscous, slippery, "slimy" fluid between the two cartilage segments, when the person is standing still. Upon initiation of walking, the surfaces begin a "hydroplaning" interaction, and thereby promote the clearing of the surface membranes for future alignment of lubricin/SAPL complexes when the joint is subsequently statically loaded.

Because of its viscous and slimy nature (and, it is hypothesized herein, because free SAPL molecules in the viscous fluid may be attracted to lubricin molecules that have become embedded in the surfaces of the cartilage membranes), the lubricating components of the synovial fluid (mainly hyaluronate and SAPL molecules) continue to keep the two cartilage segments separated from each other, so that the two opposing cartilage segments still do not directly contact each other, even if the person continues to walk or run. This is part of a natural mechanism of fluid cushioning and fluid insulation, which allows cartilage segments in knee and hip joints to remain intact, undamaged, and unabraded, despite all the wear and motion that is imposed on those joints for 70 or 80 years or more, in a healthy person.

Figure 5E:
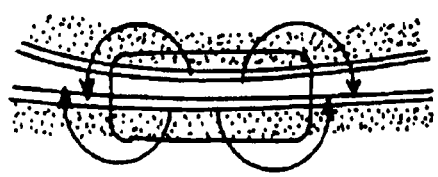

FIG. 5E depicts another apparently important factor in a "tribological" analysis of how synovial fluids can manage to successfully lubricate and protect most knee and hip joints for multiple decades. There are 4 semi-circular arrows shown in FIG. 5E. These arrows schematically depict pressures and directional fluid flows, across the two membranes that cover the femoral and tibial cartilage. These arrows indicate that, in the regions that flank the center of a high-pressure loading zone, water molecules inside the cartilage "gel" (beneath the covering membranes) in each segment of cartilage are being forced out and away from the central zone where the pressure is highest. These water molecules can flow through the gel, but they cannot do so instantaneously, because the fibrous molecular matrix that holds the gel together constrains their flow through the gel material.

As water molecules in the area of highest pressure inside a knee joint do their best to shift and flow outwardly into the flanking areas, they exert pressure against the surrounding water molecules, which fill the cartilage gel that surrounds the highest pressure region. As indicated by the arrows in FIG. 5E, this type of pressure, acting on small and mobile water molecules that are trapped inside a segment of cartilage gel, causes the semi-permeable membranes which cover the two cartilage segments in the areas that flank and surround the center zone of highest pressure to be pushed toward each other, rather than away from each other.

This type of fluid response, by small and semi-mobile water molecules trapped inside a gel, causes two important results. The first involves a more even distribution of pressure within a weight-bearing joint, such as a knee joint in a person standing upright. Since the pressures and constrained motions of water inside a cartilage gel cause the flanking and surrounding areas of cartilage to swell and press outwardly, away from their supporting bones, those flanking and surrounding regions will help support and bear a larger portion of the weight that is being imposed on that knee joint. This type of cooperative assistance, by a roughly ring-shaped (annular) circle of cartilage surrounding the center zone of maximum pressure, helps ensure that no single small area of cartilage is forced to bear the entire weight of a person's body. This type of pressure-sharing response is very useful and important, in helping prevent or minimize potentially abrasive and destructive direct contact between articulating segments of cartilage, in a knee or hip joint.

The second effect is also important, but a longer-term basis. The flow of small and mobile water molecules, within the cartilage gel, helps free embedded macromolecules (including lubricin molecules) from the semi-permeable collagenous membrane which covers a cartilage segment. In layman's terms, the motion of water molecules within and through cartilage gel may help "blow out" and rinse out the selectively permeable collagen membrane that covers a segment of cartilage. This can dislodge and remove any lubricin, SAPL, hyaluronate, or other macromolecules that have become wedged or embedded in the semi-permeable collagen membrane, and it can help prepare the membrane for subsequent interactions with fresh lubricin/SAPL complexes. This type of constrained flow of small water molecules through a gel matrix may also help generate and ensure substantially higher levels of travel and permeation of the nutrient building blocks (including glucosamine and chondroitin) through the membrane which covers a segment of cartilage gel, and through the cartilage gel itself.

All of these factors, taken together, form a model and theory of how the semi-permeable membrane that covers a cartilage segment may interact with certain components of synovial fluid.

As noted above, this invention does not rely upon that model or theory. However, this model should be considered and taken into account, by anyone who is seriously studying potential means for chemically treating a synthetic polymer to provide a slippery yet durable outer "skin" on the surface of a synthetic hydrogel that is intended as a cartilage replacement implant, since these factors and interactions can help explain why sulfonation (or possibly other similar chemical treatments) of a shallow surface layer, in a synthetic polymer hydrogel, can help create improved implants.

Another highly important factor that needs to be taken into account, in developing a useful model and understanding of how cartilage interacts with synovial fluid, involves the negative charge density on cartilage surfaces. This factor deserves separate attention in its own right.

Negative Charge Densities on Cartilage

Hyaline cartilage has a negative electrical charge, caused mainly by sulfate and carboxyl groups on the glycosaminoglycan (GAG) groups that are present in proteoglycans. This negative charge is of medical interest, because a measurable decrease in charge density implies a loss of proteoglycan density, which is a precursor and/or accompaniment to cartilage breakdown and failure. Accordingly, tracer elements have been identified (such as a compound called GD(DTPA)) that can be used, by in vivo MRI testing and similar means, to measure fixed charge density in the cartilage of patients who are suffering from joint problems.

When measured directly, using samples of cartilage taken from test animals or human cadavers, the "fixed charge density" (FCD) of human cartilage ranges from about −50 to about −250 millimolar, depending on the age of the person, and the location and condition of the cartilage (e.g., Maroudas 1979). This negative charge density, when expressed in millimolar terms, is usually measured by using a vibratome to cut cartilage into very thin slices (such as 0.2 mm thick), then weighing each layer, and then equilibrating it with a known concentration of sodium ions ($Na^+$) in a hypotonic saline solution. The amount of $Na^+$ ions that are absorbed by the cartilage, in the process of taking it to a completely neutral and uncharged state, is used to calculate the quantity that is referred to as fixed charge density. This density is then adjusted to a standard wet weight for cartilage, assuming certain equilibrium values as described in Maroudas 1979. Other ways of measuring FCD values have also been developed, and are described in articles such as Mow et al 2002, Lai et al 2000, and Van Damme et al 1992.

Since cartilage surfaces have negative electrical charges, it is presumed and believed that the "heads" of lubricin molecules have at least some localized or net positive charge, which enables the lubricin molecules to wedge their heads into the interstitial spaces between adjacent collagen fibers in a cartilage surface. Accordingly, the addition of negatively-charged sulfate groups, to a synthetic hydrogel made of a polymer such as polyacrylonitrile, will promote that same type of attraction and interaction. This addition of sulfate groups can be carried out by contacting the polymer with a sulfonating agent, such as dilute sulfuric acid, using appropriate combinations of time, temperature, and concentration.

Unless and until experimental evidence is gathered to the contrary, it is presumed and believed that the negative electrical charge density on a synthetic polymer implant should emulate the negative electrical charge density on natural healthy cartilage. Since low levels of charge density reflect proteoglycan loss and impending cartilage failure, it is generally presumed (unless and until experimental evidence indicates otherwise) that negative electrical charge densities on the articulating surface of a synthetic hydrogel implant generally should be have a "fixed charge density" within the higher regions of the naturally-occurring charge density range, such as within a range of about −100 to about −250 mM, when measured by the sodium equilibration method.

The charge density on a synthetic polymer can be altered and controlled, to any level of interest, by methods known to those skilled in the art. As simple examples, if a lower charge density is desired, a polymer surface can be treated with a lower concentration of a sulfur-donating or similar reagent, or for a shorter period of time. Alternately, if a higher charge density is desired, a polymer surface can be treated with longer treatment periods, by repetitive treatments, and/or by a series of treatments using progressively stronger reagents. Using the machinery and methods disclosed in the examples and otherwise known to those skilled in the art, samples of any such treated polymer surfaces having a range of charge densities can be tested to evaluate their wear factors, their coefficients of friction, and any other parameter of interest. By means of such tests, which will require only routine experimentation, an optimal charge density can be determined for any type of polymer of interest (such as polyacrylonitriles that have been sulfonated, phosphorylated, or otherwise treated).

The optimization of a preferred chemical treatment (which includes testing a range of temperatures, concentrations, and other conditions for carrying out a treatment, once a set of reagents has been chosen) for creating an improved surface layer will depend on the particular type of polymer that is being treated, and the particular sulfonating or other chemical reagent that has been chosen for the treatment. However, the testing of such treatment parameters is well within the skill of the art and can be carried out using no more than routine experimentation, once the goal of a surface treatment is adequately understood. This is especially true since any such surface treatment can be evaluated by comparing its results to a sulfonation treatment as disclosed herein, which can be regarded as providing a "benchmark" level of improvement in surface layers for hydrogel cartilage implants.

Examples 3-5, below, disclose methods of testing candidate surface-treated polymers, to evaluate the effects of a candidate chemical treatment on (i) the strength and durability of the resulting treated polymer, and (ii) the ability of a treated polymer to interact properly with synovial fluid. Other methods are also known to those skilled in the art.

On the subject of testing, it should be noted that the Applicants herein tested various candidate polymers, using two different fluids. One of those fluids is actual synovial fluid, from cows. Since synovial fluid is not commercially available, the Applicant and an assistant obtained it by visiting a slaughterhouse, and using a syringe to aspirate fluid from ankle joints from freshly-killed carcasses. Roughly 5 ml could be obtained from a typical ankle joint. Before use, the fluid was filtered twice through a 20 micron filter, then 0.2% w/v sodium azide as a preservative was added with stirring, it was filtered again, and then it was frozen at −20° C. until use.

Synovial fluid is not widely used by researchers and companies testing candidate materials for replacing cartilage, for two reasons. First, it is not commercially available. And second, the fact that it provides extremely good lubrication actually creates problems in those types of tests, since extremely good lubrication will tend to protect all candidate materials, making it more difficult and time-consuming to distinguish between better candidates and lesser candidates. Therefore, most researchers and companies use bovine blood serum as the lubricating liquid in such tests. Accordingly, for comparative purposes, the Applicant herein also ran various tests using bovine blood serum.

The results of the various tests described in the Examples indicated that: (i) polyacrylonitrile (PAN) polymers, and PVA/PVP polymers, both performed better if their surfaces were sulfonated; and, (ii) PAN polymers performed better than PVA polymers or PVA/PVP copolymers.

Methods of Manufacture

Any of at least four (and possibly more) alternative approaches can be used to manufacture the three-dimensional mesh which will be used to reinforce the hydrogel portion of an implant as disclosed herein.

The first approach involves weaving, knitting, or other physical interlacing of pre-existing fibers. The second approach involves crosslinking, gluing, or similar chemical treatment of pre-existing fibers. The third approach involves molding a suitable pre-polymeric compound into a shape which directly provides the desired mesh structure. The fourth approach involves using a slice of an open-cell foam.

Each approach is discussed separately, below. If desired, various combinations of those approaches can be used.

With regard to the first approach, the term "woven" is used broadly herein, and includes three-dimensional structures created from continuous fibers which are interlaced or otherwise physically interconnected, by methods such as weaving, braiding, knitting, knotting, or other comparable methods for interlacing or attaching pre-existing fibers. The term "woven" excludes polymerizing reactions or other types of chemical processing used to create strands of fiber; instead, it focuses on physical manipulation of fibers that have already been created.

As is known to those skilled in the art, different types of weaving and other fiber manipulation create materials having different traits. As one example, conventional cross-weaving generates essentially perpendicular "warp" and "woof" strands that remain nearly linear), while knitting places the fibers in more complex non-linear arrangements; as a result, knitted fabrics typically have a higher level of stretchability and elasticity than cross-woven fabrics. However, if a knitted, braided, or similar fibrous mesh is going to be embedded inside a component such as a hydrogel, the mesh can be "pre-tensioned" to some extent, or it can be treated using a cross-linking or tanning agent, to generate numerous crosslinking bonds throughout the knitted fabric; either approach can be used to stiffen a knitted, braided, or similar mesh. Accordingly, such factors and options should be taken into account in determining the exact form of weaving, knitting, or other interlacing (and any additional tensioning or other finishing or manufacturing steps) that will preferred for a particular type of fiber and/or a particular type of implant.

As used herein, "continuous fibers" can include yarn-like strands, where numerous shorter segments cling together (or have been bonded together, using covalent, ionic, or other molecular attachments) with sufficient avidity and strength to create a larger strand that has sufficient cohesion and tensile strength to allow it to function as a single unitary strand that can be woven into a larger device.

Methods and machines have been developed for carrying out three-dimensional weaving. However, in the prior art, these methods and machines apparently have not been used for creating reinforced hydrogels, for use in surgical implants. Instead, they have been used primarily to create materials and devices used in other fields, such as aerospace and military materials. A company which performs computer-controlled three-dimensional weaving is called Techniweave (Rochester, N.H.; its Internet address is www.techniweave.com). It is a subsidiary of Albany International, a producer of machinery for processing paper and other materials.

Based on a site visit to Techniweave by the Applicant herein (a surgeon who specializes in orthopedic and arthroscopic surgery), it is believed that the engineers, researchers, and process developers at Techniweave can adapt their machines and methods to create three-dimensional shapes and sizes that would render them useful as meniscal implants. The Techniweave machines and methods can be adapted to working with most types of fibers having suitable thickness and flexibility, including strands of biologically resorbable polymers as well as non-resorbable biocompatible fibers.

In the second approach to creating a mesh, a set of pre-existing fibers can be formed into a stable three-dimensional mesh by cross-linking, gluing, or similar chemical methods. One such method is similar to the polymerization process described in the Background section, but rather than using monomers that have not yet reacted to form polymeric strands, it will use pre-existing fibers, and a cross-linking agent that will bind the fibers together. For example, strands of a selected type of fiber can be stirred into or otherwise suspended in a solvent that contains a crosslinking agent. Typical crosslinking agents have two reactive groups at the opposed ends of a molecular chain having a desired length; glutaraldehyde offers an example, having reactive aldehyde groups at both ends of a three-carbon chain. Alternately, a crosslinking agent which is branched, or which has a plurality of pendant "side chains" can have more than two reactive groups. Regardless, the mixture of fiber strands and crosslinking agent are suspended together in a solvent, at a concentrations of both agents which will provide a desired final density and three-dimensional structure to the resulting crosslinked mesh. When the crosslinking reaction reaches a desired state of completion in the solvent, the entire suspension is frozen, to preserve the three-dimensional structure of the crosslinked fibers. The solvent is then removed, by a sublimizing (lyophilizing) step, using a vacuum. The crosslinked mesh that remains behind after the solvent has been removed is warmed up, and any quenching, rinsing, or other finishing steps are carried out, to form a completed three-dimensional fibrous mesh.

In the third alternate approach to creating a mesh for use herein, a hydrogel or other elastomeric material can be effectively molded into the shape of a three-dimensional mesh, by using any of several methods. In one method, two monomers are reacted while suspended in a solvent, which is then removed by lyophilization. In an alternate method, a liquid polymer or prepolymer is poured into a mold which will establish the desired three-dimensional mesh, such as with the aid of a layer of salt, sugar, or similar granular material that can be removed by a subsequent solvent treatment. In another alternate method, a liquid polymer or prepolymer is poured into a mold which will establish a three-dimensional mesh, using an "intercalating" or similar solid material that can be subsequently removed by other suitable means (such as heating, etc.). It should be recognized that this type of mesh is not comprised of fibers per se; instead, it is comprised of a highly porous network of interconnected gaps and interstitial spaces, laced throughout a material that might otherwise be relatively solid.

In the fourth alternate approach to creating a mesh for use herein, a slice of an open-cell foam can be used, as disclosed above. In this method, the relevant physical aspects (including the average pore size, and the thickness of the slice, which can be wedge-shaped if desired) must interact in a cooperative manner to provide a mesh-type structure that will reinforce and strengthen a hydrogel component, if the slice of the foam is embedded within the hydrogel.

The details of these and other suitable manufacturing techniques are known to those skilled in the art. The specific method of manufacturing is not critical to this invention; any suitable manufacturing method that will provide a three-dimensional mesh having desired levels of porosity, density, strength, and other relevant traits can be used. In general, the relevant traits of a mesh component suitable for use as disclosed herein will depend more heavily on the traits (including the diameter, flexibility, and tensile strength) of the fibers (or open-cell foam, etc.) that is selected or chemically created for use herein, than on the method used to form such fibers, foam, etc. into a three-dimensional mesh.

To create an implant for a knee meniscus, the manufacturing procedure must create a three-dimensional mesh which is thicker than just a membrane. As used herein, this implies that a mesh made of fibers must have a thickness of at least 3 layers of fibers (and preferably a substantially larger number of layers), since a relatively thick three-dimensional mesh will promotes better and more stable interlocking of the hydrogel to the mesh than can be achieved with a thin layer of fabric. As currently anticipated, an implantable meniscal device designed for an adult knee will have a thickness of about 15 millimeters (mm) at its thickest point. Since the thickest portion of a meniscal implant is around its periphery, where the implant will be anchored to the walls of the fibrous tissue capsule that surrounds and encloses the knee joint, a mesh component with a thickness that approaches or possibly even exceeds 15 mm, at the peripheral rim, may be able to give greater strength to the implant.

As briefly mentioned above, the "inner surfaces" of a meniscal wedge (these are the surfaces that will rub against femoral and tibial cartilage surfaces, inside a knee joint) should be entirely smooth, so that they will not abrade and damage the femoral and tibial cartilage. Therefore, although the mesh component may be exposed around the peripheral rim of an implant to provide improved anchoring support, the mesh preferably should remain completely hidden, and embedded, beneath any articulating surfaces that will rub against native cartilage.

Since the mesh must remain hidden and covered by a hydrogel, over a large portion of the surface area of a meniscal implant, this design is referred to herein as an "inner-mesh" design.

The "inner-mesh" design of hydrogel implants as disclosed herein offers at least three major advantages over conventional hydrogel implants. The first advantage involves greater strength and durability. These terms imply and include higher levels of any or all of the following: tensile strength, resiliency, resistance to rupture, tearing, leakage, and other loss of integrity, and ability to curtail and limit the size of a tear, cut, or other breach. These advantages arise largely from the fact that in the "inner-mesh" design, an "interpenetrating network" of fibers that pass through the gel itself can be vastly larger and stronger than the essentially "unimolecular" polymeric backbone strands that make up a conventional hydrogel. This is analogous to comparing collagen fiber bundles (which are thick and strong) to proteoglycan filaments (which are so thin they can't be seen even under the most powerful light microscopes).

The second major advantage of the "inner-mesh" design for hydrogel implants arises from the ability of the mesh component, which can be exposed around the peripheral rim of the implant, to provide greatly improved anchoring options and abilities, compared to "naked" hydrogels. Because of various factors (mainly relating to the fact that only about 2 to 5% of their volume is made of fibers, while the rest is water and dissolved molecules), hydrogels typically have low resistance to tearing and cutting. Accordingly, if a strand of suture material is poked and then laced through a hydrogel, it will tend to cut the hydrogel, in a manner comparable to a cheese cutter which uses a wire rather than a blade. It is very difficult and in many cases impossible to adequately anchor (using sutures, pins, etc.) a hydrogel in a manner suited for a permanent implant, unless a reinforcing mesh can also be provided, embedded in the hydrogel.

The third major advantage of the "inner-mesh" design for hydrogel implants arises from the response of surrounding body tissues to a fibrous or other porous structure that is exposed at the surface or positioned around all or a portion of the periphery of the implant. If a fibrous or porous structure is made from a biocompatible polymer or other material, cells from the tissue surrounding the implant will begin growing and proliferating into the mesh, forming a type of scar tissue that is, in effect, intertwined with the mesh. This process of scar tissue formation can be increased by methods known to surgeons, which involving "freshening" the contact surface of the tissue, usually by means of mild abrasion. Accordingly, the resulting ingrowth of cells and tissue into the mesh that is exposed around the periphery of a meniscal implant (or into a porous outer layer of the hydrogel or elastomeric material) can promote and enable a strong, stable, secure, and durable anchoring structure for the implant. If desired, a mesh that is exposed around the peripheral rim of an implant can be coated (using "sputter coating" or similar methods) with calcium-phosphate mixtures that emulate the apatite crystalline structure of bone, to further promote tissue ingrowth into the mesh.

All of these features contribute to the utility, strength, and durability of "inner-mesh" hydrogel implants as disclosed herein, and provide improved fixation and tissue interactions at the interface between the implant and the host tissue.

It should also be recognized that three-dimensional meshes made of fibers can be created using two or more different types of fibers. As one example, thicker fibers might be used around the periphery of a mesh component, to give maximal strength to the periphery and to any anchoring devices. As another example, fibers with clearly defined "hard" surfaces might be used in areas of the mesh that do not pass through the hydrogel component, while other types of fibers with "fuzzy" and/or swellable surfaces might be used to form the fibers that will pass through hydrogel portions. As a third example, a nonstretching fiber might be used to give a high level of strength along an axis, arc, or surface of an implant, while a different type of elastic and/or stretchable fiber might be used to provide flexibility and elastic resilience along a different axis, arc, or surface. As a fourth example, a mesh might be made of both nonresorbable fibers (made of high-strength polymers comparable to nylon) and resorbable fibers (made of collagen or various known polymers) which will gradually be degraded and digested by bodily fluids.

It also should be recognized that a flexible fibrous mesh, as that term is used herein, can be provided by a slice (which may be a wedge-shaped slice, if desired) of an open-cell foam, provided that the foam has a suitable average pore size, and the slice has a suitable thickness, so that both of those physical traits, working together, will establish a mesh-type structure that will provide suitable strengthening and reinforcing for a hydrogel material, in the types of implant disclosed herein.

A number of alternative manufacturing approaches can be used to create a hydrogel device reinforced by a mesh component. Such approaches include the following:

(i) create a complete three-dimensional mesh, then insert a pre-gelled material into it, in a manner that constrains the pre-gelled material to only a certain portion of the mesh, then polymerize that material to form the gel.

(ii) create a complete three-dimensional mesh, saturate the entire mesh in a pre-gelled material, cause the material to gel, and then remove gelled material from selected portions of the mesh, by means such as solvents, focused heating, high-pressure spray, etc.

(iii) create a gelled or pre-gelled component first, then lace a number of fibrous strands through the gel (such as while the gel is heated to make it softer and more fluid).

(iv) create a mesh component, then dip a portion of that component into a gellable material which rests inside a molding device; and/or, (v) fabricate a portion of a mesh component, add a gel component to it by means such as injection or submergence, then fabricate the remainder of the mesh component.

In addition, now that this type of composite device has been disclosed, surgeons are likely to find it adaptable and useful for various types of surgical repair in other joints, such as wrist, finger, ankle, and elbow joints.

In addition, if these materials are shown to offer exceptionally good results in those relatively accessible joints, orthopedic surgeons may be able to adapt them for use in replacing cartilage on hips. Because of the extent of tissue and vascular damage that must be inflicted on a patient's leg and hip when a surgeon removes and replaces the ball-and-socket cartilage segments that are buried deep within a hip, these implants today use relatively long and large components made primarily of steel, with a polymeric coating on one of the articulating surfaces. Because of their size and structures, it is impossible to implant these devices using minimally invasive surgery.

Because of their location and depth, it should be recognized and understood that development of relatively thin and flexible cartilage-replacing implants, for use in minimally-invasive hip surgery, poses an exceptionally difficult challenge. However, in view of the severe tissue damage suffered by patients during hip replacements, and in view of the frequency of unsuccessful outcomes (especially among elderly patients), powerful incentives exist for surgeons and researchers to try to develop minimally invasive devices and techniques, for replacing cartilage in hip joints. Accordingly, it is believed and suggested by the Applicant that the types of reinforced multi-layer implants disclosed herein offer better and more promising candidates, for such testing and research, than have previously been available.

EXAMPLES

Example 1

PVA-PVP Copolymer Samples

Granular PVA (grade 71-30, with an average molecular weight of about 140 kilodalton) was supplied at no cost by DuPont. PVP (average molecular weight about 40 kd) was obtained from Sigma Chemical. These were mixed together at a ratio of 99% PVA and 1% PVP, by weight, with a total polymer weight of 10% w/v in distilled and deionized water. The mixture was stirred for 20 minutes, by which time the solution appeared to be completely uniform and consistent. It was heated to 85° C. overnight, then cooled to room temperature, and stirred again for 20 minutes.

An aliquot of this solution was poured into a shallow flat mold, which was then kept in a warm ventilated incubator at 37° C. until essentially all water had been removed, leaving a polymeric sheet with a thickness of about 1.75 to 2 mm. This usually took about 4 to 5 days.

A punch was used to remove circular samples, usually with 0.67, 1.5, or 1.625 inch diameters, depending on the tests that were planned. Before testing, these samples were fully hydrated and swelled in aqueous phosphate-buffered saline (PBS) solution, for 1.5 to 2 days.

Several PVA/PVP samples were also formed using an alternate procedure. After overnight incubation at 85° C. as described above, a PVA/PVP solution was cooled to room temperature and then poured between glass slides that were separated at their ends by spacers with equal thicknesses. This established a consistent thickness. The samples were then frozen at –20° C. for 20 hours, then thawed to room temperature for 4 hours. This cycle was repeated 6 times, to obtain a hydrogel sheet, which was then cut into samples for testing, using a punch. The polymers formed by this method had more consistent and uniform thicknesses; however, they were not as strong and durable as the polymers formed by complete dehydration over a period of several days.

A third method of preparation was also tested, in which a combination of partial dehydration and freeze-thawing was used. This method involved pouring a quantity of the polymeric liquid into a shallow mold, to a level indicated by a mark at a fixed height, and then dehydrating the polymer at 37° C. until the level of the remaining material had decreased to the height of a lower mark. This partial dehydration was then followed by several cycles of freeze-thawing. The resulting materials were shown to have intermediate levels of strength and durability, between the fully dehydrated samples and the freeze-thawed samples, and this method offered good control over the thickness of the resulting hydrogel.

The steps that were used to sulfonate any of the above-described PVA/PVP samples were adapted from the procedures disclosed in U.S. Pat. No. 4,183,884 (Wichterle and Stoy, 1980), as follows. A solution of 60% sulfuric acid was prepared, and heated to 50° C. with stirring. If both surfaces of a PVA/PVP sample were to be sulfonated, the sample was dropped into the 60% sulfuric acid solution, for 2.5 minutes. The sample was then removed, rinsed with distilled water, dipped briefly into a mild alkaline ($NH_4OH$) solution to fully quench any remaining acid, and then rinsed again.

Because of problems were encountered when samples that were treated in this manner were tested on the tribometer, due to the high level of slipperiness on both sides of the sample, subsequent tests were done using samples that were sulfonated on only one side. This can be done in various manners, such as by placing a custom-cut sheet of polymer in the bottom of a shallow dish or tray, in a manner that causes the edges of the polymer sheet to form lips around the sides of the dish. A quantity of 60% sulfuric acid is then poured on top of the polymer layer, in a quantity that does not cause the acidic solution to spill over the edges of the polymeric sheet. The acid solution is poured off after 2.5 minutes, then the sample is rinsed, quenched, and rinsed again as described above. Samples for testing are then cut from the interior region of the sheet that was treated.

By the time the Applicant and his assistant were ready to run a complete set of tests on sulfonated PVA/PVP, so that it could be compared to non-sulfonated PVA/PVP, it had become clear to them that polyacrylonitrile polymers were providing stronger and more durable hydrogels, than PVA or PVA/PVP polymers. Therefore, a full set of comparative tests (as described below) on sulfonated PVA/PVP was not carried out.

Example 2

Polyacrylonitrile Samples

Sample sheets of polyacrylonitrile, 2.55 to 2.6 mm thick, were provided by the PragTech company (Flemington, N.J.). These sheets were of a type designated as "Qpan" by Pragtech. The exact details of the process use to manufacture the "Qpan" class of PAN are proprietary, and may be covered by one or more currently pending patent applications (including U.S. application Ser. Nos. 09/383,020 and 10/193,578, both by Stoy et al and accessible on the U.S. Patent Office website). Methods for manufacturing polyacrylonitrile are disclosed in various patents that can be located by searching for "Stoy" as the inventor, in the U.S. patent database (www.uspto.gov). Such US patents range from U.S. Pat. No. 4,107,121 ("Ionogenic hydrophilic water-insoluble gels from partially hydrolyzed acrylonitrile polymers . . . ") to U.S. Pat. No. 6,593,451 ("Method of processing polyacrylonitrile"), and include 14 additional patents in between those two. U.S. Pat. Nos. 3,895,169 and 4,183,884 also deserve mention, because they relate to surface-layer sulfonation of PAN polymers.

Circular samples of the Qpan polymer were cut from the Pragtech sheets by means of a punch. These samples were sulfonated by the same procedures disclosed above for the PVA/PVP polymers.

Example 3

Standardizing Tests on Tribometer

Before the tribometer (made by AMTI, www.amtiweb.com, and connected to a desktop computer using AMTI software) could be used for testing hydrogels, it had to be standardized, which is comparable to calibrating it. This is done using the procedures set forth in ASTM protocol F732 ("Standard Test Method for Wear Testing of Polymer Materials Used in Total Joint Prostheses").

Briefly, the tribometer machine is used to rub pins having smooth, flat-faced surfaces made of a known type of plastic, called "ultrahigh-molecular-weight polyethylene" (UHMWPE), against smooth disks made of a very hard cobalt-chromium alloy (supplied by Biomet Inc., www.biomet.com). Prior to the tests, the pins (having 0.5 inch diameters for the standardizing tests) were pre-soaked in distilled water for a month, to minimize fluid absorption during the test. A load of 253 newtons was applied to the pins, to generate an average contact stress of 3.54 megapascals (Mpa). The tribometer was programmed to move the table, which supported the discs, in a circular wear path having a 50 mm perimeter. The wear cycle frequency was 1 hertz (i.e., 1 cycle per second), giving a sliding velocity of 50 mm/s.

When a test is ready to begin, the pins are lowered onto the discs, until a known amount of force (expressed in newtons) is exerted on the pins. Based on the surface area of the pins, this generates a controllable amount of pressure (expressed in megapascals, mPa) on the UHMWPE surfaces at the bottoms of the pins. The relationship between force and pressure can be checked for accuracy by using pressure-sensitive film, such as Fuji "Pressurex" film.

Newborn bovine calf serum (ICN Biomedicals) was diluted to 50% (by volume) with distilled water and used as the lubricant. As specified by the ASTM standards, the lubricant contained 0.2% sodium azide, and 20 millimolar ethylene-diamine-tetraacetate (EDTA), as preservatives. The temperature of the lubricant was maintained at 37±1° C. throughout the test period, using a recirculating temperature control unit. The test was done for 2 million cycles, amounting to a wear path length of 100 km (about 62 miles).

After 2 million cycles, the UHMWPE plastic at the ends of the pins had an average weight loss of 24.57 mg. This converts into an average wear rate of 12.82±1.33 mm$^3$ per million cycles (mean±standard deviation), and a calculated "wear factor" of $10.1 \pm 1.05 \times 10^{-7}$ mm$^3$ per newton-meter.

These values correlate well and were close to the wear rates and wear factors of tests reported by other researchers, using UHMWPE. Accordingly, these standardizing tests confirmed that AMTI Tribometer had been set up and was working properly.

Example 4

Wear Testing of Hydrogels

Testing of hydrogels was conducted in either 100% fetal bovine serum, or 100% synovial fluid. Prior to usage in the wear tests, 0.2% sodium azide was added as an anti-bacterial agent, and the lubricant was filtered twice through a 20 micron filter. The hydrogel samples, after being attached to the pins and the discs, were soaked in the lubricant for at least two hours before the start of any test. Temperatures of all lubricants were maintained at 37±1° C. throughout the test period.

The machine can test up to 6 samples at once, each using its own pin. The hydrogel samples affixed to the pins and the discs were taken from the same sheet of material, to ensure that they had the same thicknesses. An "upper" hydrogel sample is affixed to the bottom of each pin used, using a cyanoacrylate adhesive, while "lower" hydrogel samples were attached firmly to stainless steel disks (1.7 inch diameter) with the help of acrylic fixtures. These fixtures also provide a shallow tray, which holds lubricant at a depth that will cover and bathe both of the hydrogel samples throughout a test. As mentioned above, samples that were sulfonated were treated on only one side, to allow the untreated side to provide better adhesion to the pins.

When the machine and a set of samples are ready, a force level that will be tested (usually ranging from 100 to 170 newtons) is chosen for that test. When a force of 150 newtons was applied to six pins, it generated an average contact pressure of 2.9 megapascals (Mpa), which falls within normal physiologic stress levels seen in an anatomic joint.

When the test begins, the platform that supports the stainless steel discs and the lower samples begins to move in a programmed motion. While the standardization tests used a circular motion, the wear-testing of hydrogels used a straight-line reciprocating motion, 30 mm in length. The cycle frequency was increased to 1.67 hertz, which maintained the sliding velocity at 50 mm/sec, which is the ASTM F732 standard recommendation. If a test was continued for 1 million cycles, the total sliding distance was 30 kilometers (about 18 miles).

In a typical test, samples were tested for up to half a million cycles, with occasional visual inspections at intervals that depended on the amount of force being used for that test. For example, in an initial test of sulfonated PAN using synovial fluid as the lubricant, no visible wear was detected after 487,000 cycles, at a testing force of 100 newtons; therefore, new pieces of material were tested at increasing forces of 125 newtons, then 150 newtons, then 175 newtons. The testing at 175 newtons disclosed visible wear after 120,000 cycles.

When non-sulfonated PVA/PVP hydrogels were tested, using synovial fluid lubrication, visible wear was seen after only at 4000 cycles, under an 80 newton load.

When sulfonated PVA/PVP hydrogels were tested, using synovial fluid lubrication, the samples showed significant visible wear after 2000 cycles at a 175 newton load.

When a non-sulfonated PAN sample was tested in synovial fluid, the hydrogel did not survive more than 10,000 cycles. This excessive wear was attributed to a higher friction coefficient for the non-sulfonated sample.

When sulfonated PAN was tested in synovial fluid, the gel survived 487,000 cycles at 100 newtons, with only one small scratch visible, apparently due to a tiny glue fragment that was exposed. Testing had to be stopped due to failure of the glue that held the gel to the base disc.

Subsequent testing of sulfonated PAN at loads of 125 newtons was terminated at 195,000 cycles, due to failure of the glue fixation. However, there was no visible wear on the articulating surface.

By the time these tests were finished, it was clear to the Applicant that: (i) polyacrylonitrile polymers provided more durable hydrogels than poly(vinyl alcohol) polymers; and (ii) sulfonation of the polymer surface increased the lubricity (slipperiness) of either type of polymer, and can provide a useful improvement for cartilage-replacing implants.

Example 5

Coefficient of Friction Tests

In addition to the wear tests described above, coefficient of friction values were determined for a number of hydrogel samples. These values were measured while a sample articulated against the same type of material, using either bovine blood serum or bovine synovial fluid as the lubricant, and using various force and pressure loadings. Those values are provided in Table 1.

TABLE 1

COEFFICIENTS OF FRICTION FOR HYDROGEL SAMPLES

| MATERIAL | LIQUID & LOADING | COEFF. FRICTION |
| --- | --- | --- |
| Non-Sulfonated PVA/PVP (99:1) | Blood serum, 80 newtons | 0.09–0.12 |
| Non-Sulfonated PVA/PVP (99:1) | Synovial, 80 newtons | 0.06–0.08 |
| Non-sulfonated polyacrylonitrile | Synovial, 175 newtons | 0.01–0.16 (average 0.07) |
| Sulfonated polyacrylonitrile | Synovial, 80 or 100 newtons | 0.01–0.03 |
| Sulfonated polyacrylonitrile | Synovial, 125 newtons | 0.04–0.05 |
| Sulfonated polyacrylonitrile | Synovial, 175 newtons | 0.02–0.11 (average 0.03) |

Thus, there has been disclosed herein a new design for reinforced hydrogel implants that can permanently replace injured or diseased cartilage. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Kobayashi, M. et al, "Preliminary study of polyvinyl alcohol-hydrogel (PVA-H) artificial meniscus," *Biomaterials* 24: 639-647 (2003)

Lai, W. M, et al, "On the electric potentials inside a charged soft hydrated biological tissue: streaming potential versus diffusion potential," *J Biomech Eng.* 122: 336-46 (2000)

Maroudas, A., "Physicochemical properties of articular cartilage," pp. 215-290 in M. Freeman, ed., Adult Articular Cartilage (Pitman Medical, 1979)

Mow et al, "Mechano-electrochemical properties of articular cartilage: their inhomogeneities and anisotropies," *Annu Rev Biomed Eng.* 4: 175-209 (2002)

Van Damme, E. P., et al, "The measurement of negative charge content in cartilage using a colloid titration technique," *Analytical Biochem.* 204: 250-7 (1992)

What is claimed is:

1. A surgical implant for replacing cartilage in an articulating mammalian joint, comprising:
    an anchoring surface on one side of the implant, configured for attaching the implant to a prepared surface of a bone in the articulating mammalian joint;
    a synthetic polymer hydrogel material, on a side of the implant opposite from the anchoring surface, having an exposed smooth and lubricious surface with a negative electrical charge density, adapted for lubricious sliding interactions in mammalian synovial fluid with another bone in the articulating mammalian joint, wherein the smooth and lubricious surface has a negative electrical charge density within a range of about −50 to about −250 millimolar, when measured by sodium equilibration; and,
    wherein a flexible fibrous reinforcing matrix is embedded within at least a portion of the hydrogel material.

2. The surgical implant according to claim 1, wherein the smooth and lubricious surface contains sulfur atoms.

3. The surgical implant according to claim 1, wherein the smooth and lubricious surface contains sulfonated polyacrylonitrile synthetic polymer.

4. The surgical implant according to claim 1, wherein the smooth and lubricious surface has been treated with a chemical reagent that creates crosslinking bonds between polymeric molecules.

5. The surgical implant of claim 1, wherein at least a portion of the anchoring surface comprises a porous material that promotes ingrowth of tissue after surgical implantation.

6. A surgical implant according to claim 1, wherein the synthetic polymer comprises polyacrylonitrile.

7. A surgical implant for replacing a cartilage segment that covers a hard bone surface in an articulating joint, comprising:
    a polymeric hydrogel component, at least a portion of which is reinforced by a flexible fibrous matrix, and having a smooth and lubricious articulating surface having a negative electrical charge;
    an anchoring surface on a side of the implant opposite from the smooth and lubricious articulating surface, configured to promote ingrowth of tissue following surgical implantation; and,
    a non-planar interface layer having multiple perforations, positioned between the articulating surface and the anchoring surface;
    wherein the articulating surface has a negative electrical charge density within a range of about −50 to about −250 millimolar, when measured by sodium equilibration.

8. The surgical implant of claim 7, wherein the articulating surface has been treated with a chemical reagent that creates crosslinking bonds between polymeric molecules.

9. A surgical implant for replacing a cartilage segment that covers a hard bone surface in an articulating joint, comprising:
    a polymeric hydrogel component, at least a portion of which is reinforced by a flexible fibrous matrix, and having a smooth and lubricious articulating surface having a negative electrical charge;
    an anchoring surface on a side of the implant opposite from the smooth and lubricious articulating surface, configured to promote ingrowth of tissue following surgical implantation; and,
    a non-planar interface layer having multiple perforations, positioned between the articulating surface and the anchoring surface;
    wherein the articulating surface contains sulfur atoms.

10. The surgical implant of claim 9, wherein the articulating surface has been treated with a chemical reagent that creates crosslinking bonds between polymeric molecules.

11. A surgical implant for replacing a cartilage segment that covers a hard bone surface in an articulating joint, comprising:
    a polymeric hydrogel component, at least a portion of which is reinforced by a flexible fibrous matrix, and having a smooth and lubricious articulating surface having a negative electrical charge;
    an anchoring surface on a side of the implant opposite from the smooth and lubricious articulating surface, configured to promote ingrowth of tissue following surgical implantation; and,
    a non-planar interface layer having multiple perforations, positioned between the articulating surface and the anchoring surface;
    wherein the articulating surface contains halogen atoms bonded to carbon atoms.

* * * * *